United States Patent [19]
Costello et al.

[11] Patent Number: 6,066,089
[45] Date of Patent: May 23, 2000

[54] PORTABLE REMOTE VISUAL INSPECTION SYSTEM AND A CASE AND A PERIPHERAL CARRIAGE CASE INSERT FOR TRANSPORTING AND STORING A REMOTE VISUAL INSPECTION SYSTEM

[75] Inventors: James G. Costello, Huntington; Joseph K. Leo, Farmingdale; Peter Lorenz, Massapequa; Eugene McGarry, Greenlawn; Hiroshi Tanoue, Commack; Gordon Randall Perry, New York; Joel Hoag, Brooklyn, all of N.Y.

[73] Assignee: Olympus Optical Co., Ltd., Japan

[21] Appl. No.: 08/907,588

[22] Filed: Aug. 8, 1997

[51] Int. Cl.[7] .................................................. A61B 1/00
[52] U.S. Cl. ..................... 600/102; 206/363; 348/838; 312/7.2
[58] Field of Search ................................ 600/102, 178; 348/65, 68, 72, 73, 838, 836, 839; 312/7.2, 290, 223.5, 328; 242/396.5, 396.6, 400, 407; 206/363, 438

[56] References Cited

U.S. PATENT DOCUMENTS

| | | | |
|---|---|---|---|
| 3,072,452 | 1/1963 | Sleeper | 312/290 |
| 4,238,086 | 12/1980 | Brimmeier | 242/296.7 |
| 4,398,212 | 8/1983 | Serry | 348/836 |
| 4,525,746 | 6/1985 | Mangold | 348/839 |
| 4,741,627 | 5/1988 | Fukui | 374/208 |
| 4,755,881 | 7/1988 | Barlett | 348/838 |
| 4,854,301 | 8/1989 | Nakajima | 600/102 |
| 4,933,816 | 6/1990 | Hug | 600/178 |
| 4,998,282 | 3/1991 | Shishido | 600/102 |
| 5,090,259 | 2/1992 | Shishido et al. | |
| 5,161,028 | 11/1992 | Kawata | 358/254 |
| 5,314,070 | 5/1994 | Ciarlei | 242/172 |
| 5,348,222 | 9/1994 | Patey | 312/290 |

FOREIGN PATENT DOCUMENTS

| | | | |
|---|---|---|---|
| 9405345 | 10/1994 | Germany | 600/178 |
| 4-81711 | 3/1992 | Japan . | |
| 5-56486 | 8/1993 | Japan . | |

*Primary Examiner*—John P. Leubecker
*Attorney, Agent, or Firm*—Michaelson & Wallace; Peter L. Michaelson

[57] ABSTRACT

A device, having a case body and case lid, for use with a remote visual inspection system. The case body is adapted to accommodate a light source for providing light to the remote visual inspection system. The case lid is adapted to cover the case body, and to accommodate a video display monitor for displaying an image captured by the remote visual inspection system.

33 Claims, 20 Drawing Sheets

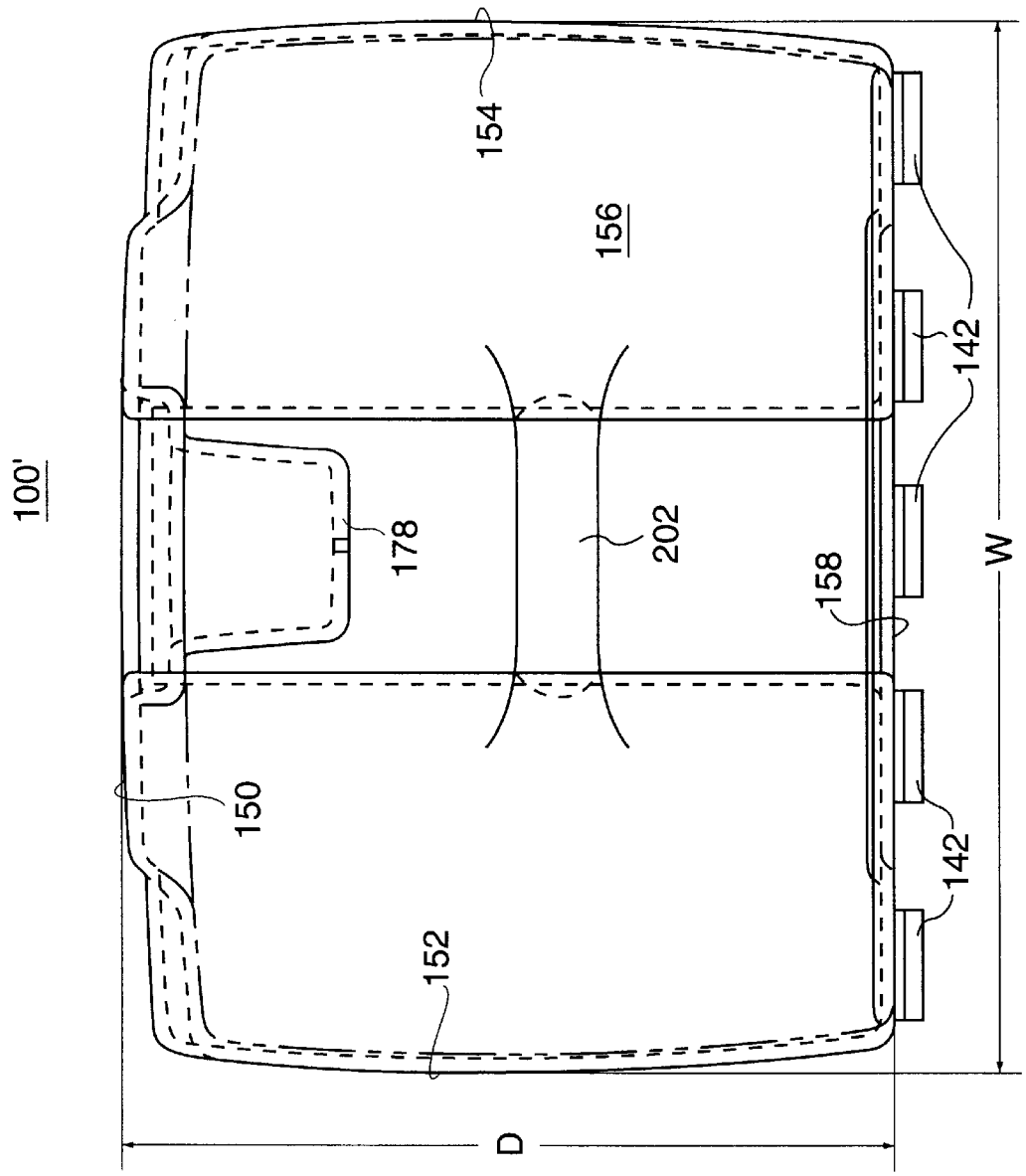

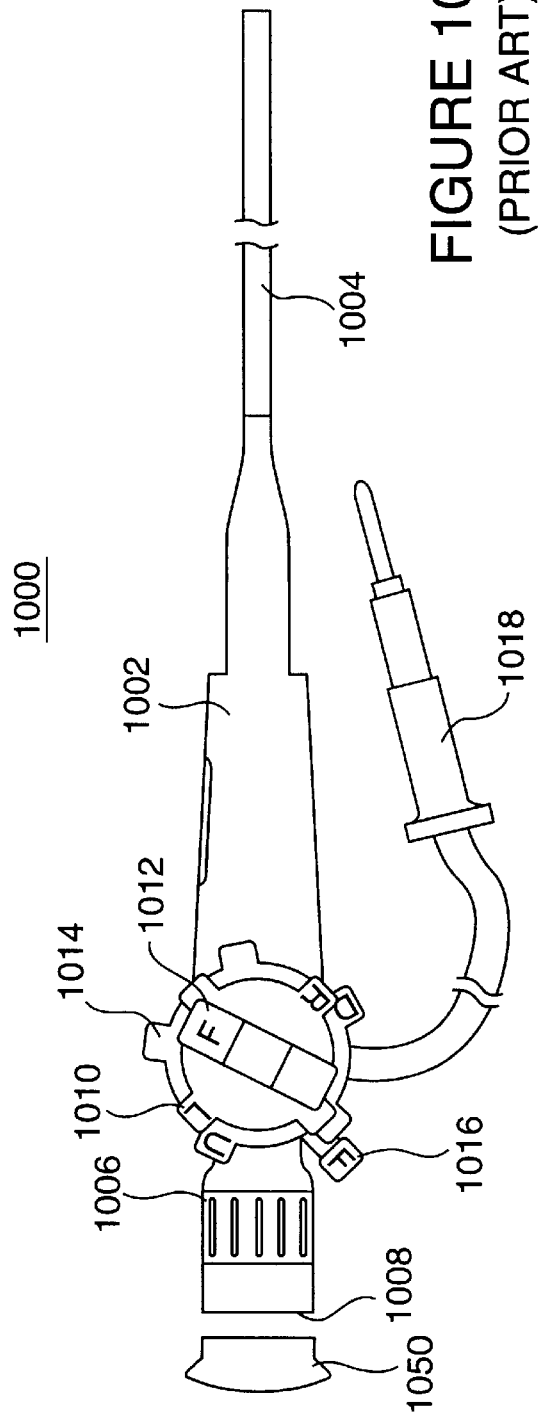
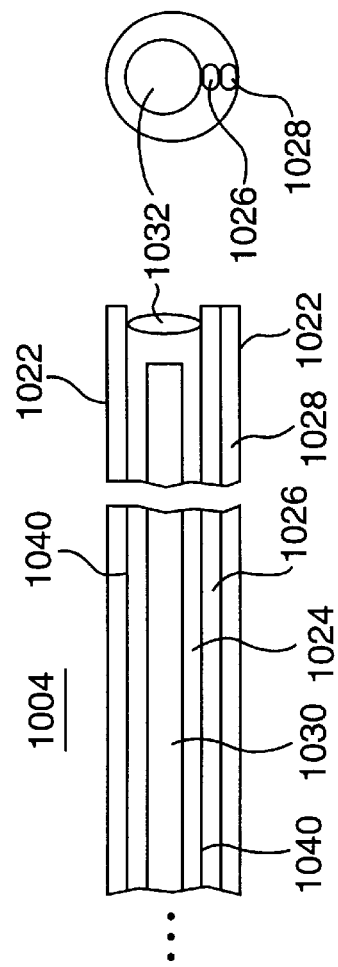
FIGURE 10A (PRIOR ART)
FIGURE 10B (PRIOR ART)
FIGURE 10C (PRIOR ART)

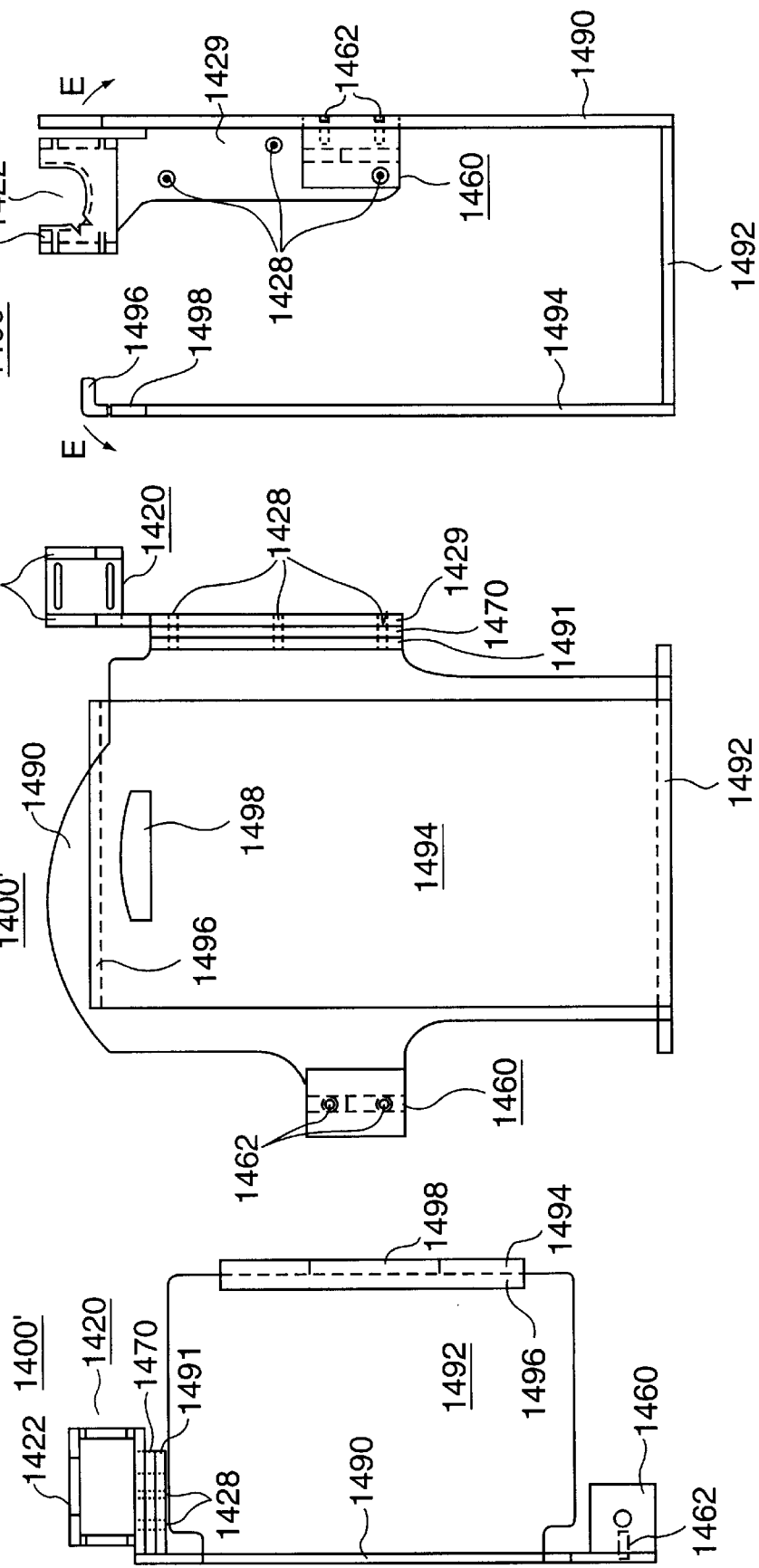

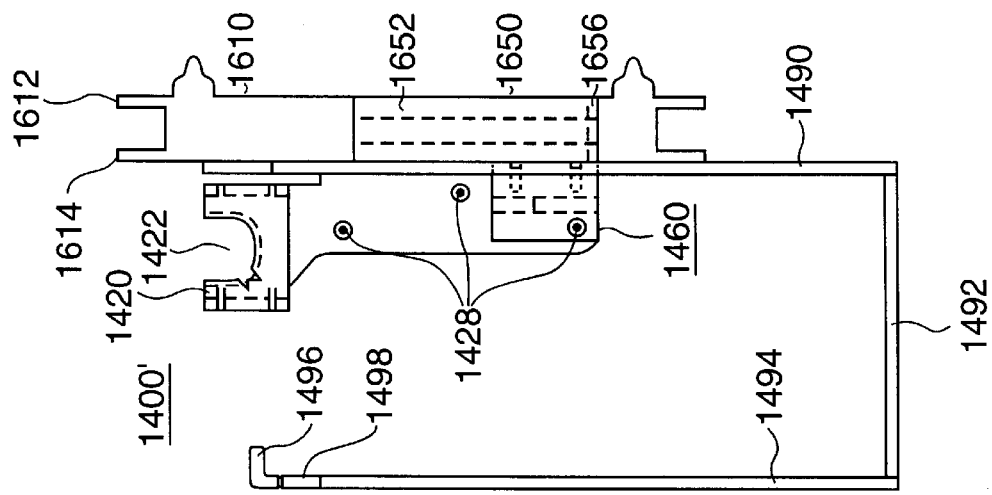
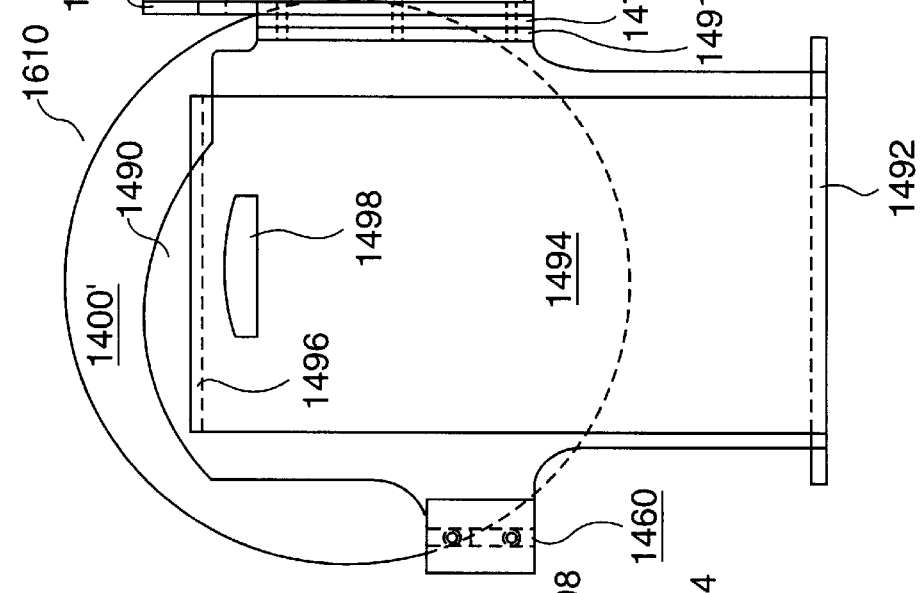
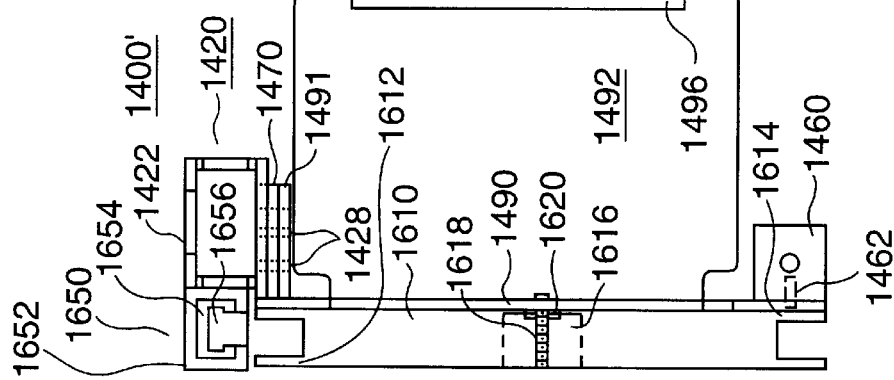

PORTABLE REMOTE VISUAL INSPECTION SYSTEM AND A CASE AND A PERIPHERAL CARRIAGE CASE INSERT FOR TRANSPORTING AND STORING A REMOTE VISUAL INSPECTION SYSTEM

BACKGROUND OF THE INVENTION a. Field of the Invention

The present invention concerns remote visual inspection systems, and in particular, concerns a case (and/or a peripheral carriage case insert) for transporting and storing remote visual inspection systems.

b. Related Art

Remote visual inspection systems have enjoyed wide use in industrial applications and in the medical field. In industrial applications, remote visual inspection systems are used for inspecting difficult to access parts, such as the turbine blades of a jet engine enclosed in an engine housing for example. In the medical field, remote visual inspection systems (e.g., endoscopes) are used for medical diagnosis (e.g., of the gastrointestinal tract) and for visual feedback during surgery.

Remote visual inspection systems, such as flexible fiberscopes and flexible videoimagescopes for example, include an insertion tube. In industrial applications, the insertion tube may be inserted through an inspection port or a small opening of a machine. In medical applications, the insertion tube is inserted through a small incision or a body orifice. In each case, the insertion tube relays an image, received at its distal end, which is within a machine housing or a patient's body, to its proximal end, which is outside of the machine housing or patient's body.

Although one skilled in the art understands the features and operation of flexible fiberscopes and videoimagescopes, a brief description is provided below for the reader's convenience.

FIG. 10a is a side view of a flexible fiberscope 1000. The flexible fiberscope 1000 includes a body 1002 and an insertion tube 1004. The insertion tube 1004 is flexible such that its distal end may be articulated left and right, by means of left-right articulation control 1010, and up and down, by means of up-down articulation control 1014. The left-right articulation control 1010 may be locked by brake 1012, while the up-down articulation control 1014 may be locked by brake 1016. The body 1002 also includes a diopter adjusting ring 1006 and an eyepiece 1008. An adapter (not shown) may be used to connect a video camera (not shown) to the eyepiece 1008. A cap 1050 covers the eyepiece 1008 when the fiberscope 1000 is not in use. Finally, a light guide connector 1018 permits connection to an external light source.

FIG. 10b is a cross-sectional side view, and FIG. 10c is an end view, of the distal end of the insertion tube 1004 of the flexible fiberscope 1000 of FIG. 10a. Wall 1022 defines an outer cylinder and wall 1040 defines an inner cylinder. Within the space 1024 defined by the inner cylinder, a bundle of coherent optical fibers 1030 carries an image focused at its distal end by an objective lens 1032. A fiberoptic or liquid light guide 1026, which serve as illumination means, and working channels 1028 which can accommodate sensors and/or tools, are located between the inner and outer cylinders.

FIG. 11a is a side view of a flexible videoimagescope 1100. As with the flexible fiberscope 1000 discussed above, the flexible videoimagescope 1100 also includes a body 1102 and a flexible insertion tube 1104. The distal end of the flexible insertion tube 1104 may be articulated left and right, by means of left-right articulation control 1108, and up and down, by means of up-down articulation control 1112. The left-right articulation control 1108 may be locked by brake 1110, while the up-down articulation control 1112 may be locked by brake 1114. Finally, a light guide and video cable 1118 permits connection to an external light source, via connector 1120, and to a camera control unit, via connector 1122.

Unlike the flexible fiberscope 1000 discussed above, the videoimagescope 1100 does not have focus or diopter adjustment rings, nor does it have an eyepiece. This is because, as alluded to above, the videoimagescope 1100 provides a video output to an external camera control unit. More specifically, as shown in FIG. 11b, which is a partial cut-away, perspective view of the distal end of the videoimagescope 1100 of FIG. 11a, an objective lens 1150 focuses an image 1158' of an object 1158 in its field of view 1156, onto an imaging device, such as a charge coupled device (or "CCD") 1152 for example. The CCD 1152 (and associated circuitry) provides a sequence of analog waveforms based on the charge accumulated in each element of the CCD array. The camera control unit, mentioned above, converts the sequence of analog waveforms to frames of video, which comply with the NTSC, PAL or S video standard for example.

As is further shown in the perspective view of FIG. 11b, the distal end of the insertion tube 1104 of the videoimagescope 1100 includes an illumination window 1132 passing light from a light guide 1130, as well as a working channel 1140 terminating at port 1142.

Peripheral devices, such as a video monitor, a light source, working tools, printers, video tape recorders, and other storage devices may be used to enhance the functionality of remote visual inspection systems.

Although remote visual inspection systems have become indispensable in many industrial and medical applications, their use in the field has been limited by the weight and bulk of these systems, together with needed peripheral devices. Further, certain elements of the remote visual inspection system, as well as peripheral devices, must be protected from shock and extreme environmental conditions. Finally, for field use to be optimized, the time to deploy the remote visual inspection system, along with any needed peripheral devices, must be minimized.

As shown in FIG. 8, wheeled carts 800 have been used to transport visual inspection systems within a given facility. The wheeled cart 800 may include an adjustable video monitor mount 802, a pivoting keyboard tray 804, and shelves 806 for holding peripheral equipment. Although such wheeled carts 800 are extremely useful for transporting remote visual inspection systems within a single facility, particularly those facilities having elevators, such as most hospitals for example, their transport function is not optimized for use among geographically separated sites or for use in the field (e.g., flight line, chemical process tank, and agricultural farm).

As shown in FIG. 7, reels 700 have been used to store and transport relatively long (e.g., 36 feet to 52 feet) insertion tubes 706 of remote visual inspection systems. The reel 700 may include a front plate 702 and a rear plate 704, between which a rotatable drum (not shown) is disposed. The insertion tube 706 is wound around the rotatable drum. The reel 700 may also include a floor stand 708, a handle 710 for one handed manual transport, handles 714 for two handed manual transport, and buckles 712 for preventing the rotation of the drum and plates. Although the reel 700 is useful for carrying and storing long insertion tubes, its functionality is limited in that it does not store other elements of the remote visual inspection system or peripheral devices.

FIG. 9 illustrates an improved reel 900 having a foam storage piece 920 for storing components and connectors of a remote visual inspection system. As was the case with the reel 700, the reel 900 may include a front plate 902 and a rear plate 904, between which a rotatable drum (not shown) is disposed. The insertion tube 906 is wound around the rotatable drum. The reel 900 may also include a floor stand 908, a handle 910 for one handed manual transport, handles 914 for two handed manual transport, and buckles (not shown) for preventing the rotation of the drum. The foam storage piece 920 includes cut-outs 922 for holding components and connectors of a remote visual inspection system. For example, cut-out 922*a* can accommodate the body 1002 of a flexible fiberscope 1000, cut-out 922*c* can accommodate the body 1102 of a videoimagescope 1100, cut-out 922*e* can accommodate the camera control unit connector 1122 of a videoimagescope 1100, cut-out 922*f* can accommodate a light guide connector, and cut-outs 922*b*, 922*d*, and 922*g* can accommodate tip adapters and other miscellaneous components and connectors. Although the reel 900 offers increased functionality over the reel 700 discussed above, it is not designed to carry peripheral devices such as a light source, a camera control unit, a video display monitor, etc. Moreover, the reel 900 should be placed in a separate case during extended transport during which it may be subjected to shock and environmentally harsh conditions.

Although the above described cart 800 and reels 700/900 are useful for storing and transporting remote visual inspection systems under certain conditions, a better storage and transport means would expand the types of applications for remote visual inspection systems. For example, if an improved storage and transport means were available, off-site service companies could easily visit different industrial sites of different companies to periodically inspect machines. Moreover, a company with geographically remote facilities could have a central inspection department which would visit the remote facilities for periodic inspections, thereby better utilizing the company's investment in remote visual inspection equipment. Finally, specially trained medial teams could administer emergency medical help in the field in response to an accident or disaster.

The improved storage and transport means (e.g., a case) should permit easy storage and transport of a remote visual inspection system. Naturally, the weight and bulk of the improved case should be minimized. Further, the improved case should preferably be able to store and transport peripheral equipment. More specifically, the improved case should store and transport the most commonly used peripheral equipment such as long insertion tubes, video monitors, light sources, and camera control units. Moreover, the improved case should permit quick deployment of the remote visual inspection system and its peripheral devices. The case should be rugged and protect the remote visual inspection system and peripheral devices from harsh environmental conditions as well as bumps and shocks. Finally, the cost of the improved case should be minimized to the extent possible.

SUMMARY OF THE INVENTION

The present invention expands the functionality of the known reels and carts, and expands the possible applications of remote visual inspection systems by providing a case, having a body and a lid, for storing and transporting a remote visual inspection system. The case body accommodates a light source for providing light to the remote visual inspection system. The case lid is adapted for covering the case body, and accommodates a video monitor for displaying an image captured by the remote visual inspection system. The case lid may be pivotably coupled, for example with a hinge system, with the case body. The hinge system may include a constant torque hinge or a ratchet hinge.

The case body may include a main body section and a hinged body section which is pivotably coupled with the main body section. The main body section may accommodate the light source. The hinged body section may include a reel for holding a flexible insertion tube of the remote visual inspection system which can be generated in place and/or deployed and operated outside the case.

The present invention also includes a portable remote visual inspection system having a remote visual inspection system and a case. The case includes two sections. A first section of the case accommodates a light source for providing light to the remote visual inspection system. The second section of the case is coupled with the first section of the case, and accommodates the remote visual inspection system. The second section of the case may also include a reel which holds a flexible insertion tube of the remote visual inspection system.

The present invention also provides a portable drum (e.g., a reel) for holding an insertion tube of a remote visual inspection system. The portable drum (e.g., reel) includes a case body, a reel, and a lid. The drum (e.g., reel) is rotatably coupled with the case body such that, at any given time, a first portion of the drum (e.g., reel) is located within a cavity defined by the case body and a second portion of the drum (e.g., reel) extends outside of the cavity defined by the case body. The lid is adapted for covering the case body and the reel. The lid may be pivotably coupled with the case body. In one embodiment, when the lid is shut so as to cover the case body, the lid prevents the drum (e.g., reel) from rotating with respect to the case body.

The weatherproof case body may include a front wall, a back wall, a left side wall arranged between the front and back walls, and a right side wall arranged between the front and back walls. The walls define an upper end of the case body and a lower end of the case body The lower end of the case body is closed by a bottom surface. The back wall may be taller than the front wall such that the left and right walls are tapered. The drum (e.g., reel) is preferably rotatably coupled with the front wall.

The lid may include a back wall, pivotably coupled with the back wall of the case body, a front wall, a left side wall arranged between the front and back walls of the lid, and a right side wall arranged between the front and back walls of the lid. The front, back, left side, and right side walls of the lid define an upper end of the lid and a lower end of the lid. The upper end of the lid is closed by a top surface. The front wall of the lid is taller than the back wall of the lid such that the left and right walls of the lid are tapered.

Finally, the present invention discloses a device for transporting and storing a remote visual inspection system. The device includes a case body and a lid. The case body is configured to accommodate a light source and an insertion tube. The lid can be pivotably coupled with the case body and is configured to accommodate a video display monitor.

The device may include a removable case body insert (or "peripheral carriage") for accommodating peripheral devices. The removable case body insert may include at least one connector holder. In one embodiment, the removable case body insert includes a front plate, a rear plate, and a bottom plate arranged between the front plate and the rear plate. The front plate and/or rear plate of the removable case body insert may have a handle to permit the removable case body insert to be easily inserted into and removed from the case body. The front or rear plate may be provided with (i) a rotatable reel or drum for accommodating an endoscope insertion tube (ii) an endoscope body holster and/or (iii) a positionable video display screen. The front plate of the removable case body insert may include a rearwardly extending ledge. In this case, an inside surface of a front section of the lid includes a lip which abuts the ledge of the front plate of the removable case body insert when the lid is closed upon the case body thereby limiting movement of the case body insert within the case body.

The device may include a removable drum for accommodating an insertion tube of a remote visual inspection system. The removable drum may be a reel which includes a front plate, a rear plate, and an annular element arranged between the front and rear plates of the removable drum. The annular element may be compressible foam and may be provided with a defined slot.

The case body may include a main body section and a hinged body section. The main body section is configured to accommodate the light source. The hinged body section is pivotably coupled with the main body section and is configured to accommodate the insertion tube. The hinged body section preferably includes a drum (e.g., reel), rotatably coupled with an inside surface of the hinged body section. The drum (e.g., reel) is configured to accommodate the insertion tube.

The main body section may include a back wall, a left side wall adjacent to the back wall, a right side wall adjacent to the back wall, a floor adjacent to the back, left side, and right side walls, and an insert. The insert has an outer surface shaped to fit within the back wall, the left side wall, the right side wall, and the floor, and has a first inside surface configured to accommodate the light source.

The hinged body section may include a front wall, a left side wall adjacent to the front wall, a right side wall adjacent to the front wall, a floor adjacent to the front, left side, and right side walls of the hinged body section, and a reel. The drum (e.g., reel) is rotatably coupled with the front wall of the hinged body section and adapted to accommodate the insertion tube.

The insert of the main body section may include at least one indent to accommodate at least one of (i) an auxiliary video connector, (ii) light source connectors, and (iii) a camera control unit connector. Moreover, the insert is preferably shaped such that, when a light source is accommodated by the insert, connection ports and controls of the light source are visible and accessible.

The floor of the main body section may be pivotably coupled with the floor of the hinged body section.

The lid may include a front wall, a back wall, a left side wall arranged between the front and back walls of the lid, a right side wall arranged between the front and back walls of the lid, a top surface, closing a top edge of the front, back, left side, and right side walls of the lid, and an insert. The insert of the lid has an outer surface shaped to fit within a cavity defined by the front wall, the back wall, the right wall, the left wall, and the top surface of the lid, and has an inner surface shaped to accommodate the video display monitor.

The insert of the lid and/or the insert of the main body section may be a foam insert.

The device of the present invention has three states; namely, a fully closed state, a partially opened state, and a fully opened state. In the first, fully closed weatherproof state, (i) the hinged body section is closed against the main body section such that the left wall of the hinged body section abuts the left wall of the main body section and the right wall of the hinged body section abuts the right wall of the main body section, and (ii) the lid is closed against the case body such that the left wall of the lid abuts the left walls of the main body section and the hinged body section, the right wall of the lid abuts the right walls of the main body section and the hinged body section, and the front wall of the lid abuts the front wall of the hinged body section.

In the second, partially opened state, (i) the hinged body section is closed against the main body section such that the left wall of the hinged body section abuts the left wall of the main body section and the right wall of the hinged body section abuts the right wall of the main body section, and (ii) the lid is opened from the case body such that the left wall of the lid is separated from the left walls of the main body section and the hinged body section, the right wall of the lid is separated from the right walls of the main body section and the hinged body section, and the front wall of the lid is separated from the front wall of the hinged body section.

In the third, fully opened state, (i) the hinged body section is opened from the main body section such that the left wall of the hinged body section is separated from the left wall of the main body section and the right wall of the hinged body section is separated from the right wall of the main body section, and (ii) the lid is opened from the case body such that the left wall of the lid is separated from the left walls of the main body section and the hinged body section, the right wall of the lid is separated from the right walls of the main body section and the hinged body section, and the front wall of the lid is separated from the front wall of the hinged body section.

When the case is in its first, fully closed state, the drum (e.g., reel) of the hinged section compresses the insert of the lid and/or the insert of the main body section. When the case is in its second, partially opened state, the insert of the main body section is compressed by the drum (e.g., reel) of the hinged body section.

BRIEF DESCRIPTION OF THE DRAWINGS

FIG. 2b is a plan view.

FIG. 10a is a side view of a conventional flexible fiberscope. FIG. 10b is a cross sectional side view of a section of the insertion tube and distal end of the flexible fiberscope shown in FIG. 10a. FIG. 10c is an end view of a tip adapter at the distal end of the flexible fiberscope shown in FIG. 10a.

FIG. 11b is a perspective view of the distal end of the videoimagescope shown in FIG. 11a.

FIG. 14a is a plan view, FIG. 14b is a front end view, and FIG. 14c is a side view of a main body insert (also referred to as a "peripheral carriage") for the case of FIGS. 13a through 13d.

FIG. 16a is a plan view, FIG. 16b is a front end view, and FIG. 16c is a side view of an alternative main body insert (also referred to as a "peripheral carriage") similar to that shown in FIGS. 14a–14c but for use with a simple case.

DETAILED DESCRIPTION

The present invention concerns a novel and non-obvious portable remote visual inspection system and a case for transporting, storing and deploying as a compact platform, a remote visual inspection system. The following description is presented to enable one skilled in the art to make and use the invention, and is provided in the context of particular embodiments. Various modifications to the described embodiments will be apparent to those skilled in the art, and the general principles set forth below may be applied to other embodiments and applications. Thus, the present invention is not intended to be limited to the embodiments shown.

Figure 1:
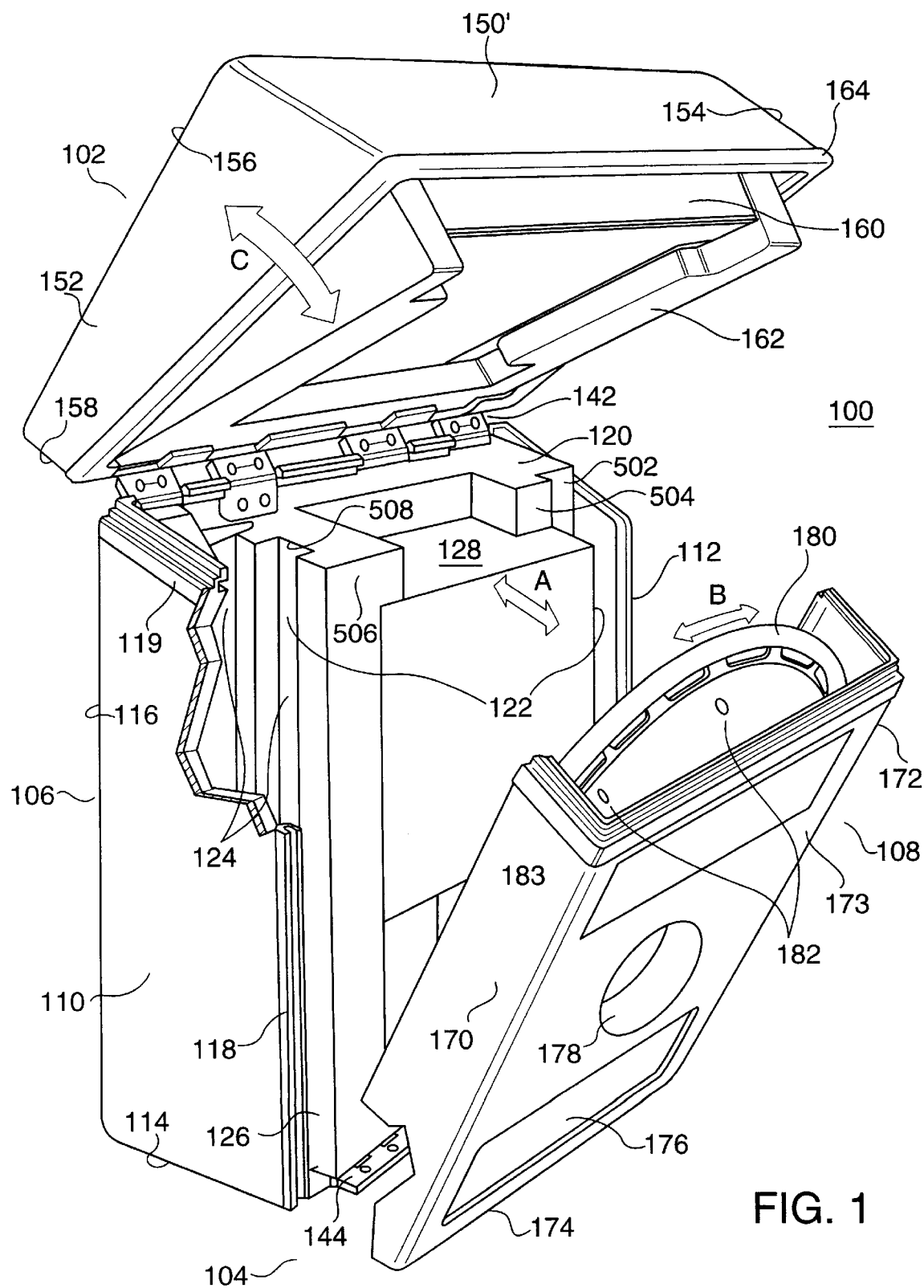
FIG. 1 is a perspective and partially disassembled view of a first embodiment of the case of the present invention.

FIG. 1 is a perspective and partially disassembled view of a first embodiment of the case 100 of the present invention. The case 100 includes two main components; namely, a case lid 102 and a two-piece case body 104. The two-piece case body 104 includes a main body section 106 and a hinged body section 108. The case lid 102 is pivotably connected with the main body section 106 by means of a hinge system 142, such as one or more constant torque or rachet hinges for example. Thus, the case lid 102 can pivot with respect to the main body section 106 in the directions shown by arrows C. The main body section 106 is pivotally connected with the hinged body section 108 by means of a hinge system 144, such as one or more spring hinges for example. Thus, the hinged body section 108 can pivot with respect to the main body section 106 in the directions shown by arrows A. Each of the components of the case 100 is discussed in more detail below.

Figure 2A:
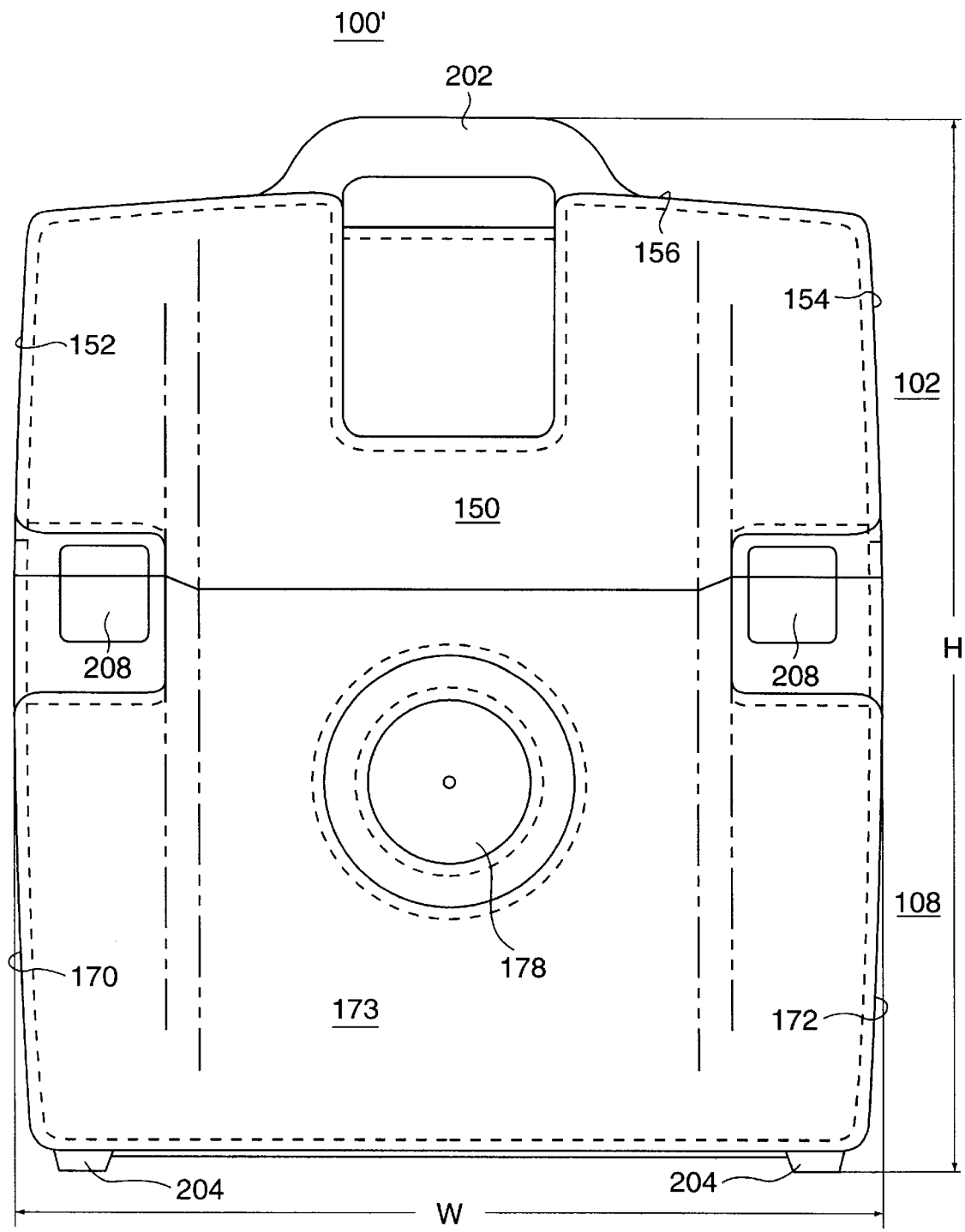
FIG. 2a is a front end view.
Figure 2C:
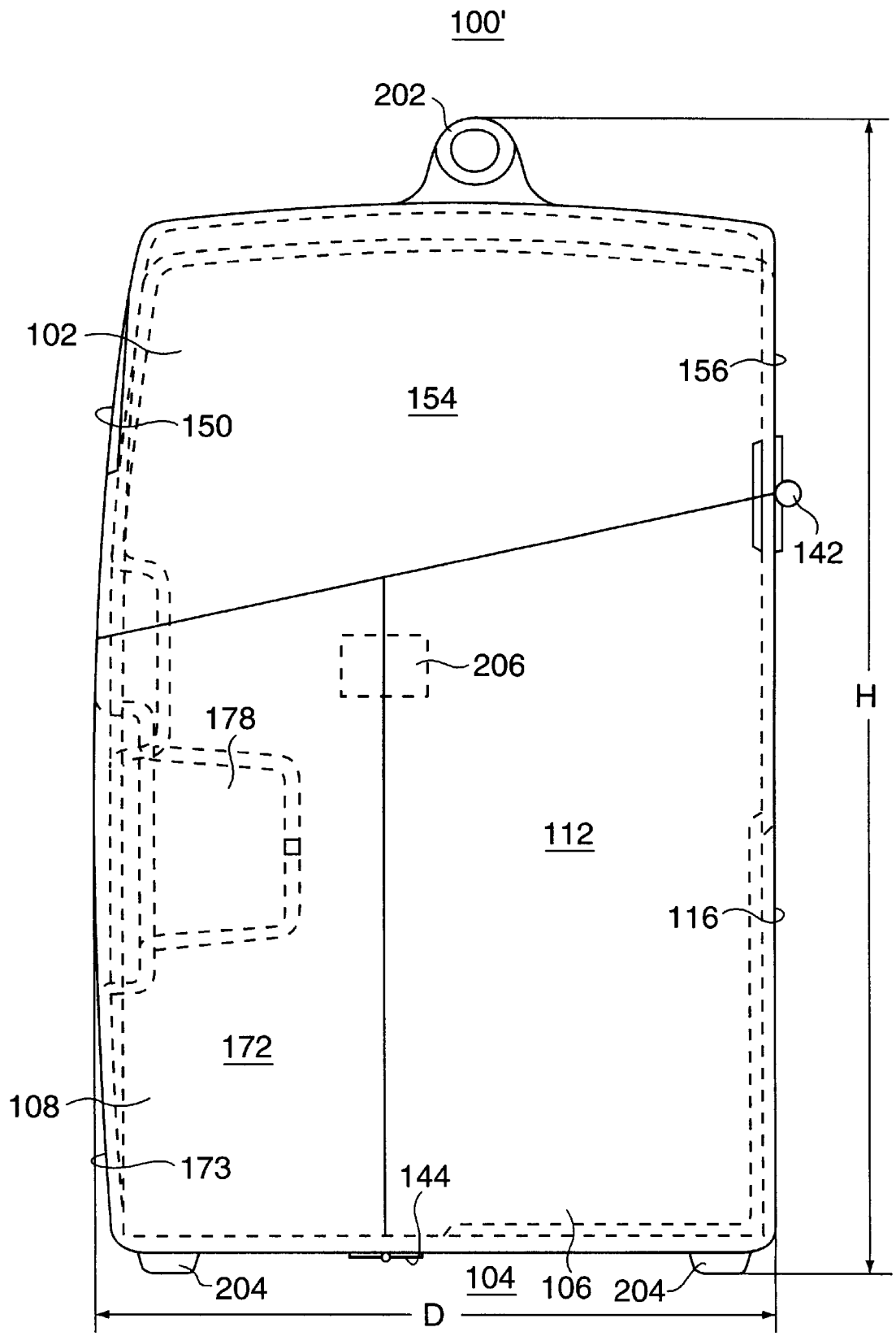
FIG. 2c is a side view of the case of FIG. 1.

As shown in FIGS. 1, and 2a through 2c, the case lid 102 includes an outer shell having a front wall 150, a left side wall 152, a right side wall 154, a top surface 156, and a back wall 158. The outer shell is preferably made from a hard plastic which may be molded in a known manner. A metal piece 164 (e.g., a rectangular aluminum piece having a u-shaped cross section) is fixed (e.g., glued, stamped, fastened, and/or friction fit) to the otherwise exposed edges of the front, back, and side walls. As shown in FIGS. 2a through 2c, the lid may include a handle 202.

Figure 3:
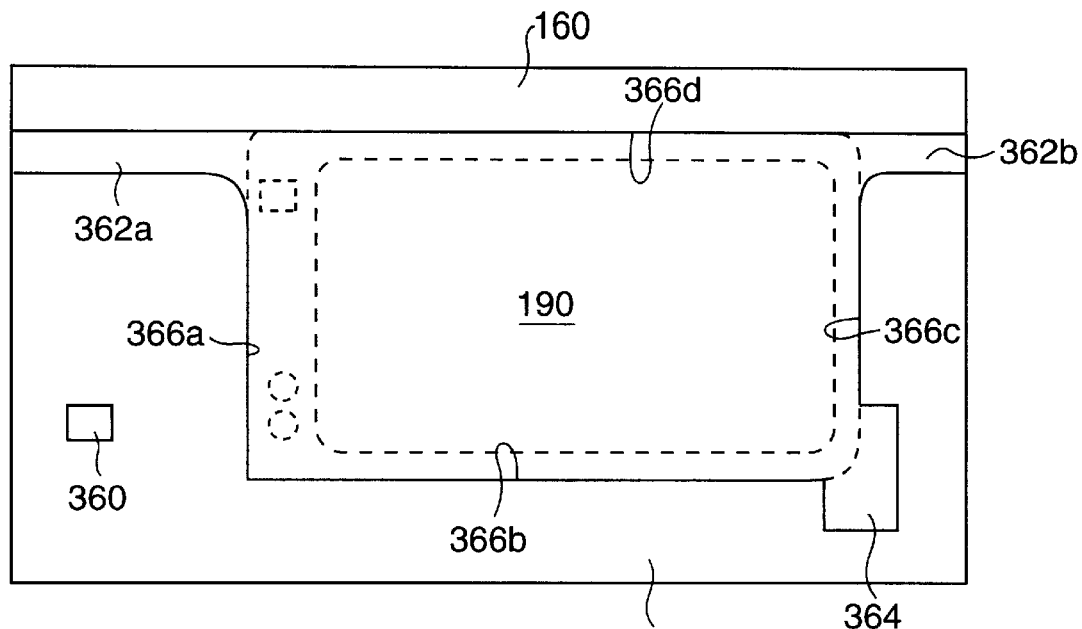
FIG. 3 is a plan view of a foam insert(s) of a lid of the case of the present invention.

Foam insert(s) are preferably provided within the cavity defined by the inner surface of the shell of the lid 102. In this case, first 160 and second 162 foam inserts are provided. The first and second foam inserts 160 and 162 are preferably slightly compressed by the cavity defined by the inner surface of the shell of the lid 102 such that they are securely held in place. Alternatively, the first and second foam inserts 160 and 162 may be glued or otherwise fastened to the inner surface of the shell of the lid 102. As shown more clearly in the plan view of FIG. 3, the first and second foam inserts 160 and 162 preferably define surfaces 366 (shown as 366a, 366b, 366c and 366d) for securely holding a flat panel video monitor 190 (e.g., a 10.4" flat panel LCD monitor sold by Olympus Optical Co., Ltd. of Tokyo Japan as item no. OVD1; shown in phantom). The foam insert 162 may include a cut-out 360 for a power plug connector for supplying power to the video display monitor 190. Spaces 362a and 362b defined between the first 160 and second 162 foam inserts, as well as cut-out 364, permit a video monitor 190 to be grasped from the side or the rear to facilitate removal of the video monitor 190 from the case lid 102. Naturally, insert(s) of different materials and/or configurations for performing similar functions may be used.

As shown in FIGS. 1, and 2a through 2c, the main body section 106 includes an outer shell having a left side wall 110, a right side wall 112, a bottom surface 114, and a back wall 116. The outer shell of the main body section 106 is preferably made from a hard plastic. A metal (e.g., aluminum) piece 119 is fixed (e.g., glued, stamped, fastened, and/or friction fit) to the otherwise exposed upper edges of the back and side walls of the main body section 106 and mates with the metal piece 164 of the lid 102. Further, a metal piece 118 (e.g., an aluminum piece having a groove (or tongue)) is fixed to the otherwise exposed front edges of the side walls of the main body section 106. The metal pieces 118 and 119 may be an integral metal piece.

Figure 4:
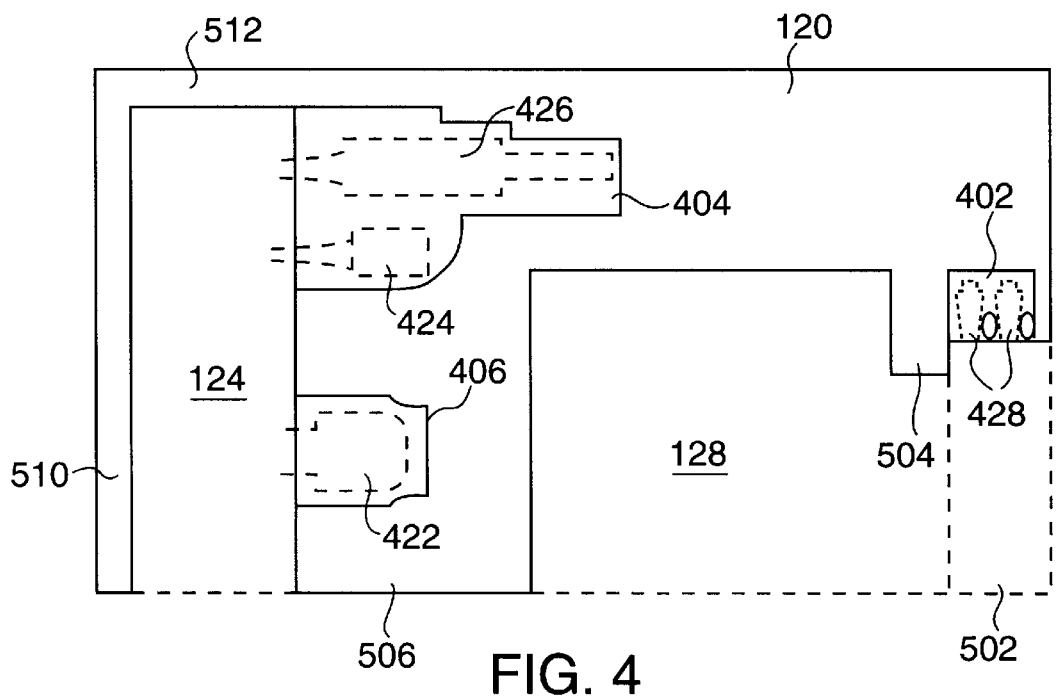
FIG. 4 is a plan view of a foam insert(s) of a main body section of the case of the present invention.
Figure 5:
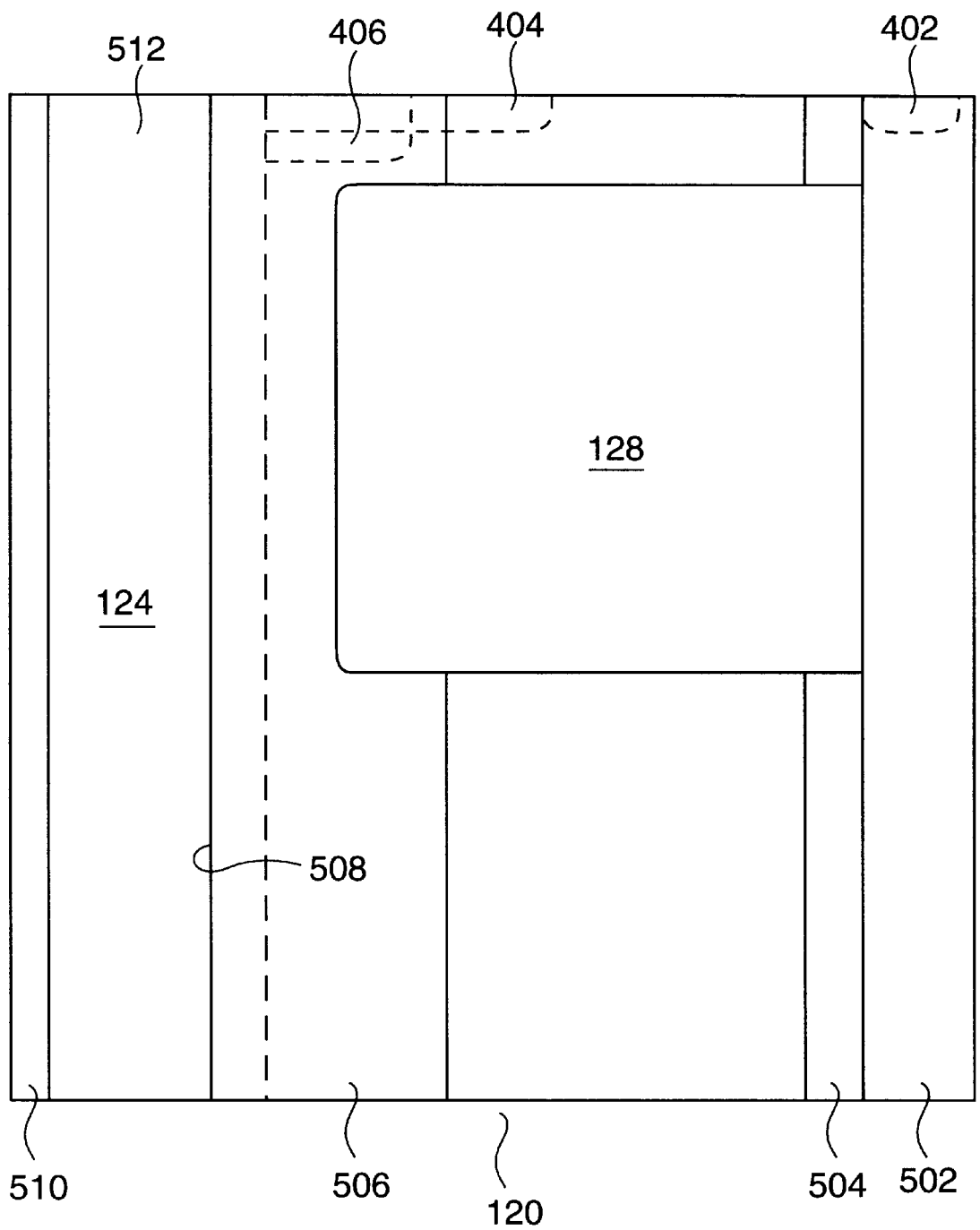
FIG. 5 is a front end view of the foam insert(s) of FIG. 4.

As shown in FIGS. 1, 4, and 5, a foam insert 120 is provided within the main body section 106. As shown in FIGS. 4 and 5 (but not shown in FIG. 1 for clarity), a top surface of the foam insert 120 may include recesses 402, 404, and 406. The recess 402 is shaped to accommodate auxiliary video output (e.g., "S-VIDEO OUT" or "COMPOSIT BNC VIDEO OUT") connectors 428. The recess 404 is shaped to accommodate the two (2) connectors 424 and 426 of a light source guide. The recess 406 is shaped to accommodate a camera control unit connector 422.

As shown in FIG. 4, the foam insert 120 includes a first extension 504, a second extension 506, a back wall section 512, and a left wall extension 510. A recess 124, which may be used to store various cords, is provided between the second extension 506, the back wall section 512, and the left wall extension 510 of the foam insert 120. As shown in FIGS. 1 and 5, the extensions 504 and 506 are notched to accept peripheral equipment 128 (preferably an integrated light source and camera control unit, such as model no. ILVC1 sold by Olympus America of Melville, N.Y. for example). Vent recesses 502 and 508 permit the flow of air and heat when the peripheral equipment 128 is operating.

The hinged body section 108 includes an outer shell having a left side wall 170, a right side wall 172, a front wall 173, and a bottom surface 174. The outer shell of the hinged body section 108 is preferably made from a hard plastic. A metal (e.g., aluminum) piece 183 is fixed (e.g., glued, stamped, fastened, and/or friction fit) to the otherwise exposed upper edges of the front and side walls of the hinged body section 108 and mates with the metal piece 164 of the lid 102. Further, a metal piece (e.g., an aluminum piece having a tongue (or groove); not shown) is fixed to the otherwise exposed rear edges of the side walls and mates with the groove (or tongue) of the metal edge 118 of the main body section 106.

The front wall 173 of the hinged body section 108 may include a recess 176 for accommodating a shipping label. The front wall 173 may also define a circular recess 178 which forms a circular extension (See FIGS. 12a and 12b.) on the inside surface of the hinged body section 108. The circular extension defines an axis about which a drum (e.g., reel) 180 may rotate as shown by arrows B. The drum (e.g., reel) 180 may accommodate a relatively long insertion tube (e.g., up to 52 feet or more), the tip of which may be held in one of the holders 182 defined in the reel 180. Alternatively, the tip of the insertion tube may be held in a recess of a foam insert (e.g., one of foam inserts 160, 162, or 120 discussed above) or wedged between two foam pieces of a foam insert.

Figure 12A:
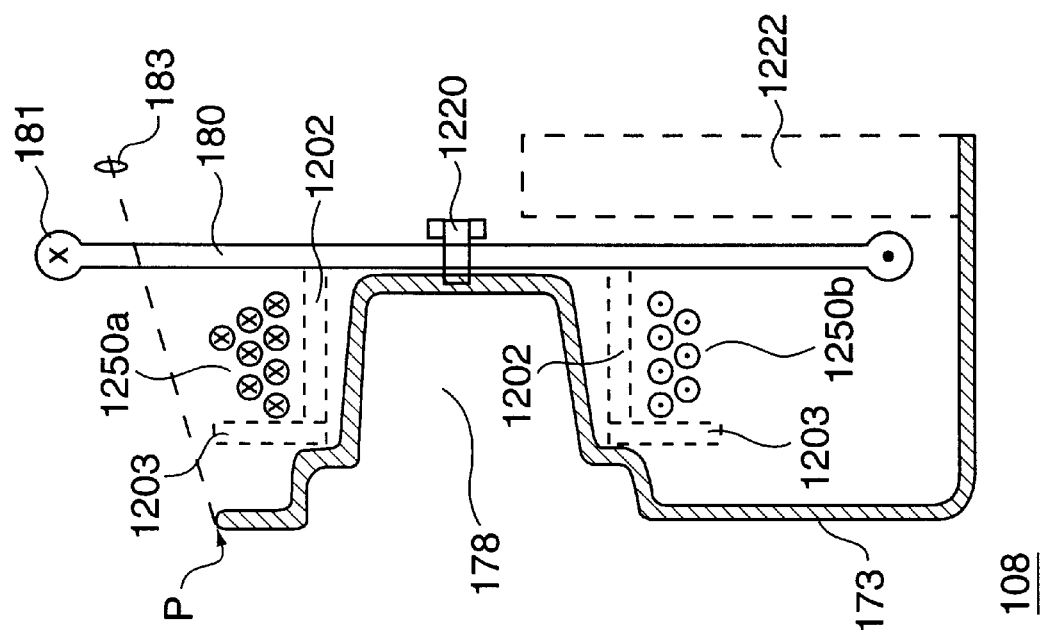
FIGS. 12a and 12b are cross-sectional side views of alternative hinged body sections of the case of FIG. 1.
Figure 12B:
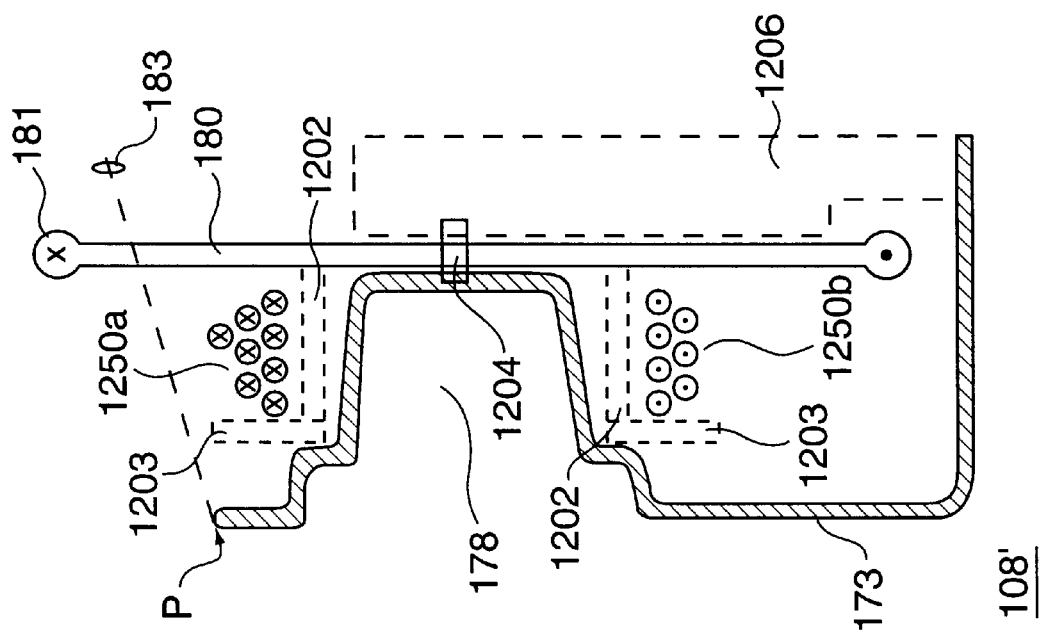

FIGS. 12a and 12b are cross-sectional side views which illustrate alternative embodiments of the hinged body section 108 and 108'. As shown in FIG. 12a, the reel 180 may be rotatably coupled with the indent 178 of the front wall 173 of the hinged body section 108 by means of a shaft 1220, such as a bolt for example. The means with which the reel 180 is rotatably coupled with the hinged body section 108 preferably provides such an amount of friction that the reel 180 may be rotated by hand but, free spinning of the reel 180 is prevented.

An optional cylindrical extension 1202 may be provided to support a wound insertion tube 1250 (shown in split cross-sections 1250a and 1250b). The radius of the cylindrical extension 1202 may be larger than that shown. However, the diameter and length of insertion tubes wound around reels 180 having cylindrical extensions 1202 of larger diameter are limited. In any case, the outer radius of the cylindrical extension 1202 should be at least as great at the maximum bending radius of curvature of the insertion tube 1250. The cylindrical extension 1202 may be provided with an optional circular plate (or flange) 1203. In this case, the reel 180 may be removed from the hinged body section 108. In this way, different insertion tubes, pre-wound on a reel 180, may be mounted on to the hinged body section 108.

A foam wall 1222 having recesses (not shown) may be provided so that additional elements of the remote visual inspection system or peripheral equipment may be stored. The foam wall 1222 is preferably sized to compress against the reel 180 and the peripheral equipment 128 stored in the main body section 106 when the case 100 is shut to further prevent the reel 180 from free spinning and to minimize shifting of the peripheral equipment 128 during transport.

The alternative embodiment of the hinged body section 108 shown in FIG. 12b is similar to that shown in FIG. 12a. However, in the alternative embodiment, the member 1206 can support the shaft 1204. Thus, the shaft 1204 may be held by the member 1206 or by both the member 1206 and the front wall 173 of the hinged body section 108.

As can be seen in both FIG. 12a and FIG. 12b, the top of the reel 180 defines a handle 181 which extends beyond the top of edge P of the metal piece 183 at the front wall 173. This spacing permits the reel 180 to be spun by hand from the front of the case 100. Moreover, when the case 100 is closed, the foam insert 160 (see, e.g., FIG. 1) of the lid 102 is partly compressed by the top of the reel 180 such that free spinning of the reel 180 is further limited.

In general a "drum" is a cylindrical body, while a "reel" is a spool and may be thought of as a drum with extending front and rear walls. However, the use of the term "reel" should be broadly interpreted to include a drum for example.

As shown in FIG. 2a, latches or other locking means 208 may be provided on the front walls 150 and 173 of the lid 102 and the hinged body section 108, respectively, to prevent the lid 102 from being opened (See arrows C of FIG. 1) during storage or transport. As shown in FIG. 2c, latches or other locking means 206 may be provided on the left and right side walls of the main body section 106 and hinged body section 108 to prevent the hinged body section 108 from being opened from the main body section 106 (See arrows A of FIG. 1). In a preferred embodiment, the latches 206 are provided on the inner surfaces of the left and right sides of the main body and hinged body sections so that they cannot be unlatched until the lid 102 is opened. Moreover, the latches 206 are preferably provided close to the top edges of the left and right sides of the main body and hinged body sections so that they are more visible and easy to reach.

As shown in FIGS. 2a and 2c, the case 100 may be provided with feet 204 on the bottom surfaces 114 and 174 of the main body section 106 and the hinged body section 108, respectively.

Figure 6:
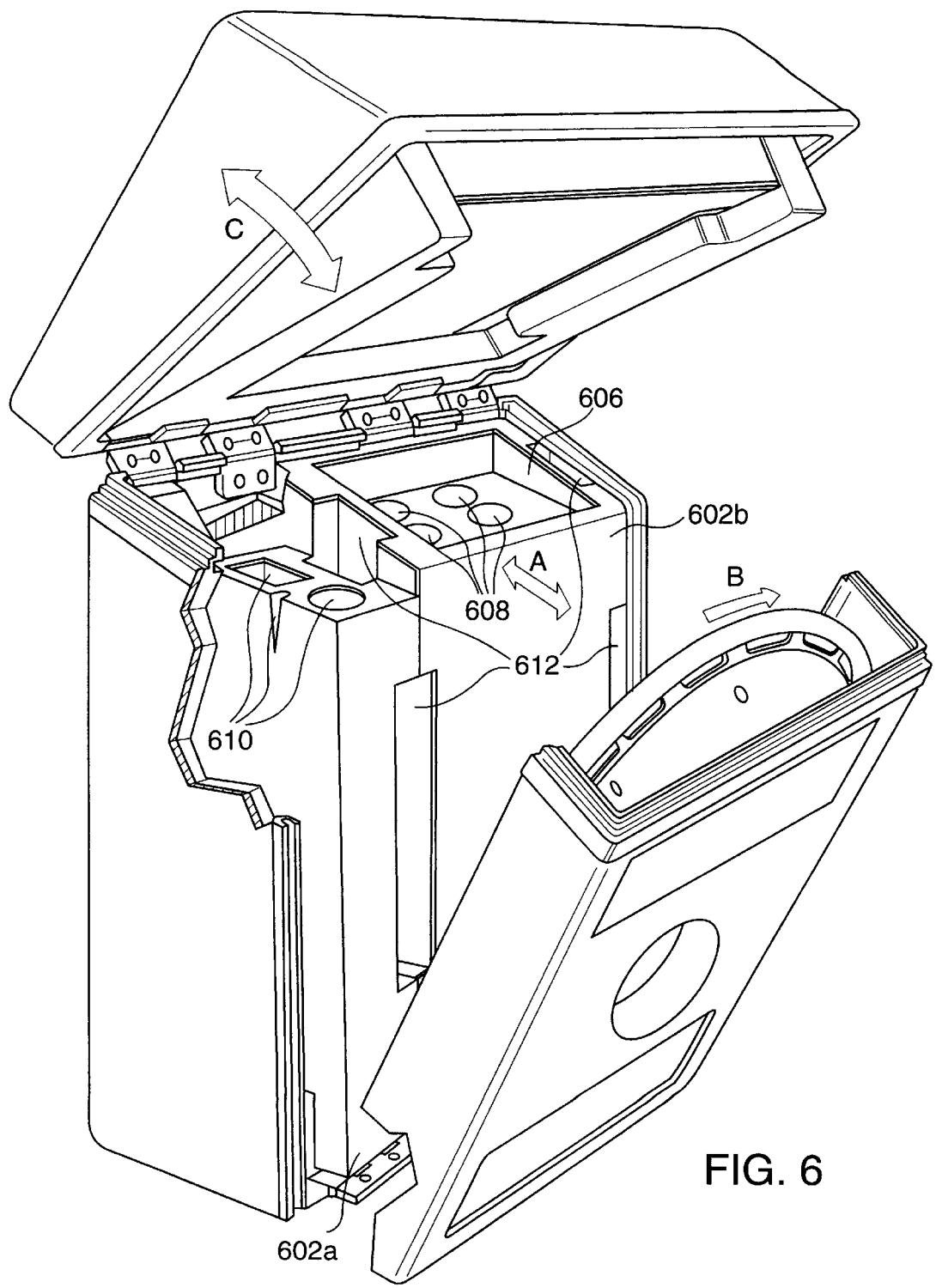
FIG. 6 is a perspective and partially disassembled view of a second embodiment of the case of the present invention.
Figure 8:
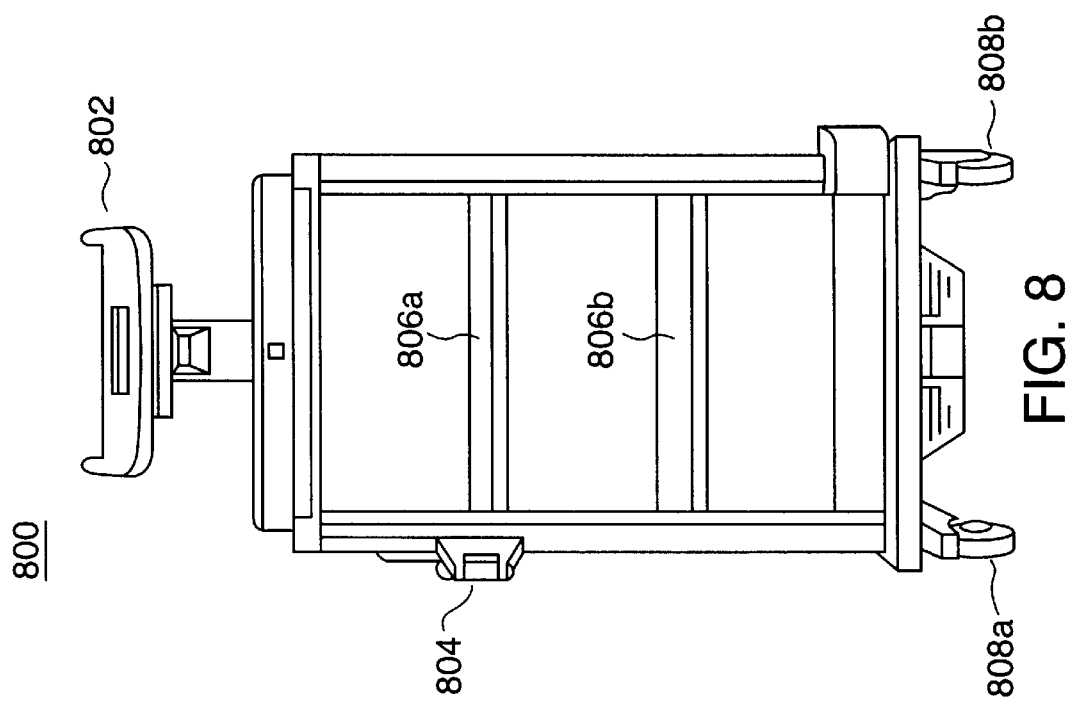
FIG. 8 is front end view of a cart for carrying a remote visual inspection system and peripheral equipment.
Figure 7:
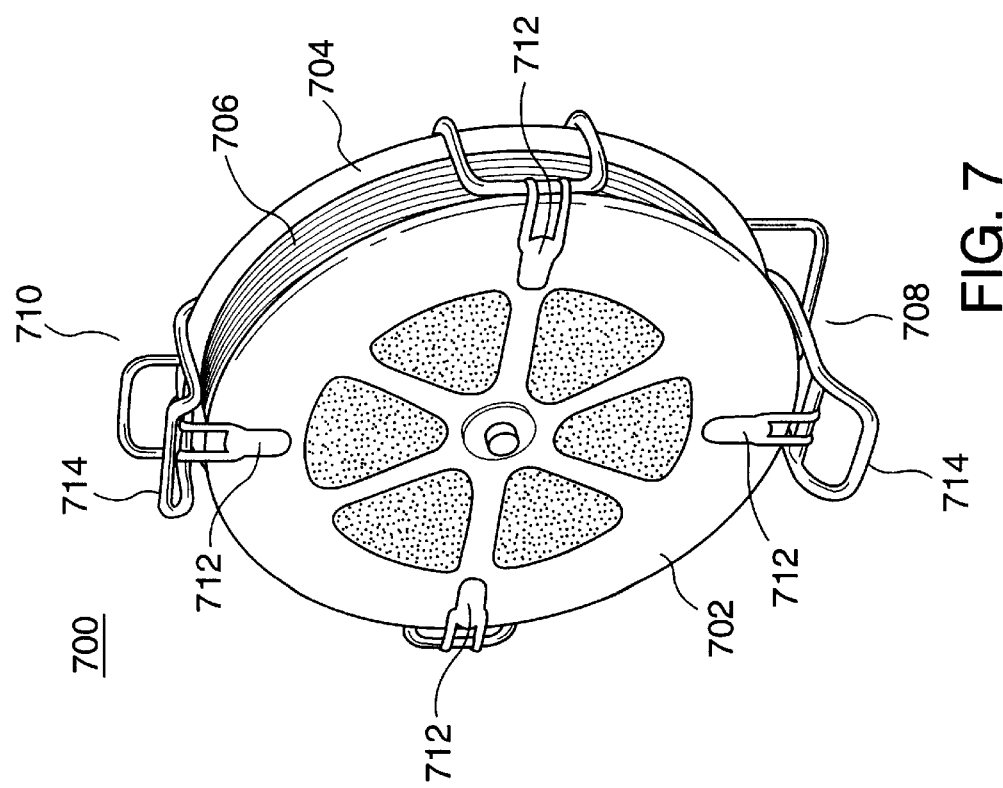
FIG. 7 is a perspective view of a reel for carrying a relatively long insertion tube of a conventional remote visual inspection system.
Figure 9:
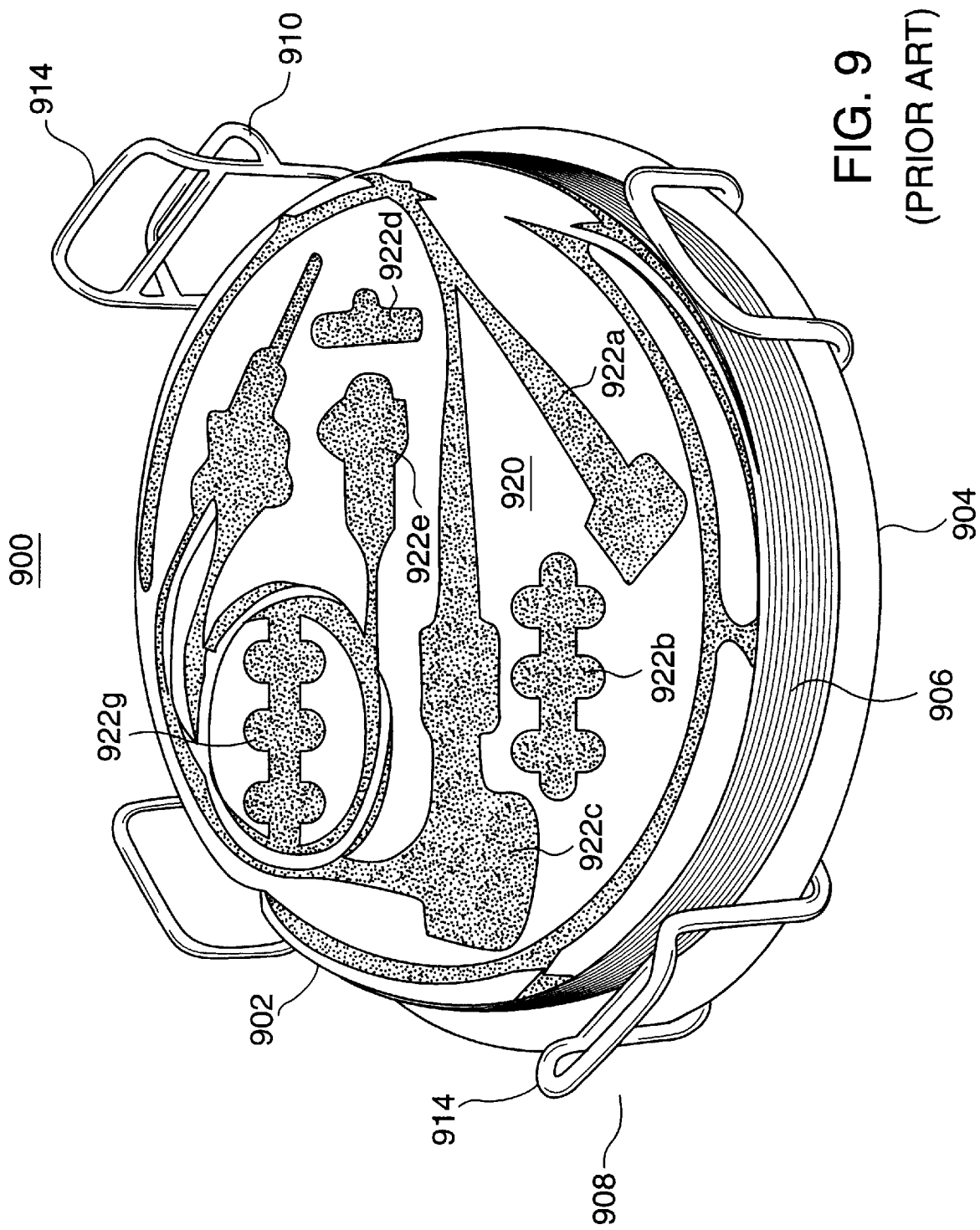
FIG. 9 is a perspective view of a conventional reel for carrying a remote visual inspection system including a relatively long insertion tube.

The second embodiment 600 of the case of the present invention shown in FIG. 6 is basically identical to the case 100 shown in FIG. 1. Accordingly, similar elements are not labeled and described here. However, in the embodiment 600, shown in FIG. 6, of the case of the present invention, the insert(s) 602 replace the foam inserts 120. As shown in FIG. 6, the insert 602 may include a first insert 602a and a second insert 602b. The second insert 602b may include a recess 606 having cut-outs 608. The cut-outs 608 permit access to connectors and/or controls of peripheral equipment (not shown) stored in the main body section of the case 600. The insert 602a may include recesses 610 for accommodating light source connectors, a camera control unit connector, and tip adapters, for example. Voids 612 defined between the first and second inserts 602a and 602b, and between the second insert 602b and the right side wall of the main case section permit the flow of air and heat so that the peripheral equipment does not overheat during operation. Other voids may be defined to hold cables and other recesses may be defined in the inserts to accommodate other elements of a remote visual inspection system and its peripheral equipment.

When the lid 102 is opened, the video display monitor (not shown) can be viewed, controls and connection ports at the top of the peripheral equipment 128 can be accessed easily, and connectors and/or other elements of the remote visual inspection system accommodated in the top of the foam insert 120 can be accessed easily. Moreover, due to the clam-shell design of the case body 104, when the hinged body section 108 is pivoted away from the main body section 106, controls and connection ports at the front of the peripheral equipment 128 can be easily accessed. Thus, once the case 100 is transported to a field site, the remote visual inspection system can be quickly set up. Moreover, when done, the remote visual inspection system can be quickly stored. Finally, the case can accommodate a flat panel display monitor, peripheral equipment, and a relatively long insertion tube.

Figure 13A:
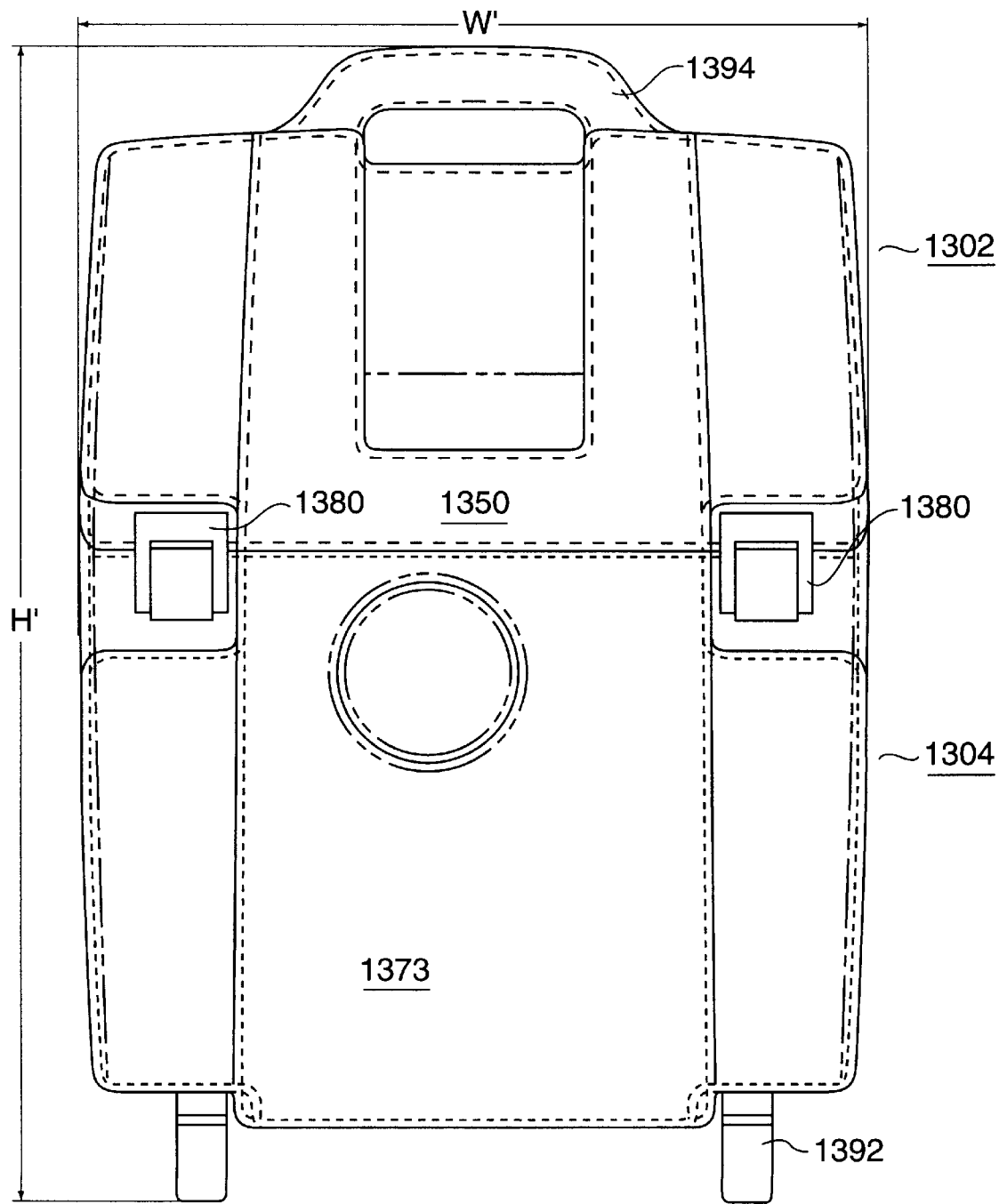
FIG. 13a is a front view.
Figure 13B:
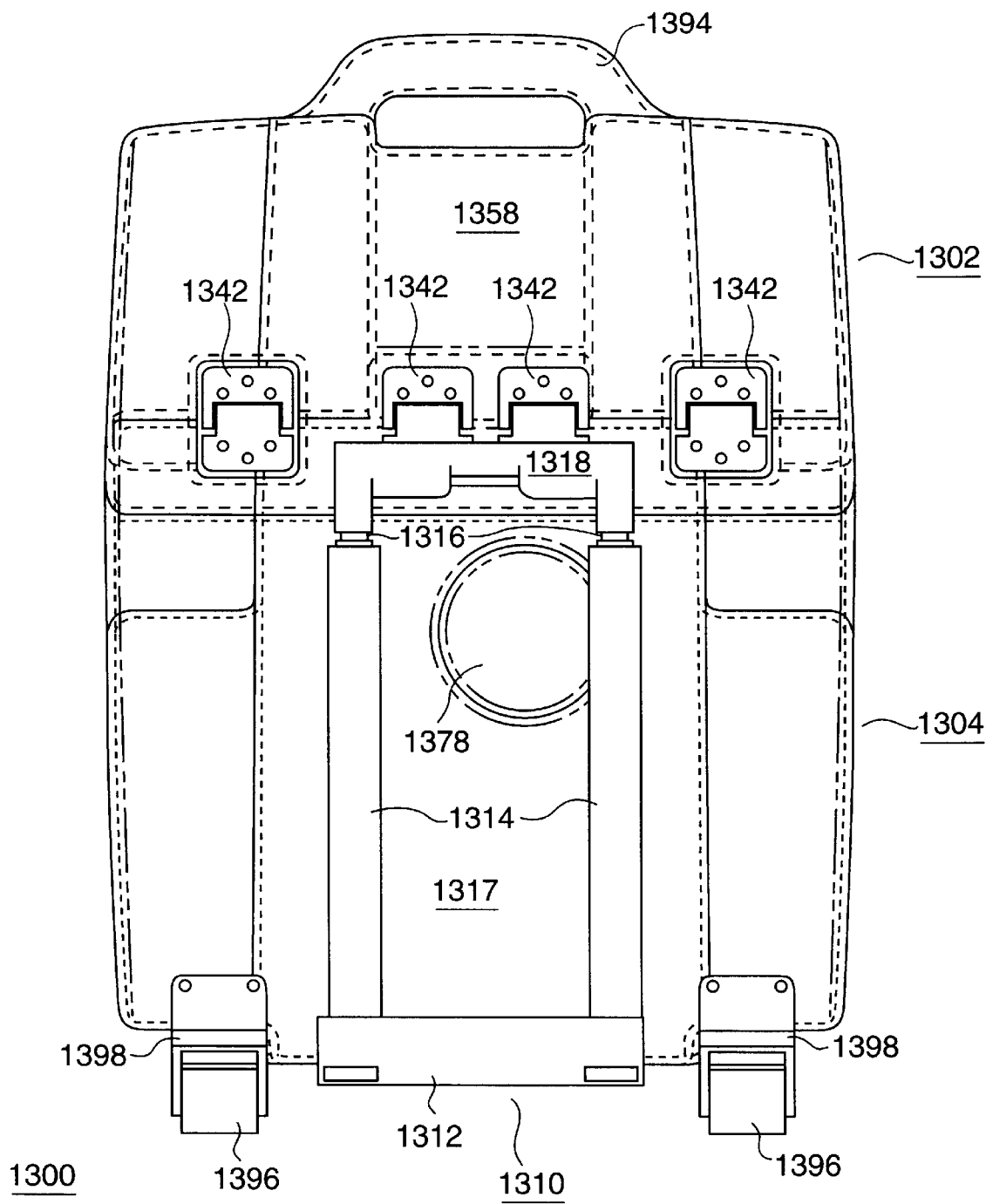
FIG. 13b is a rear view.
Figure 13C:
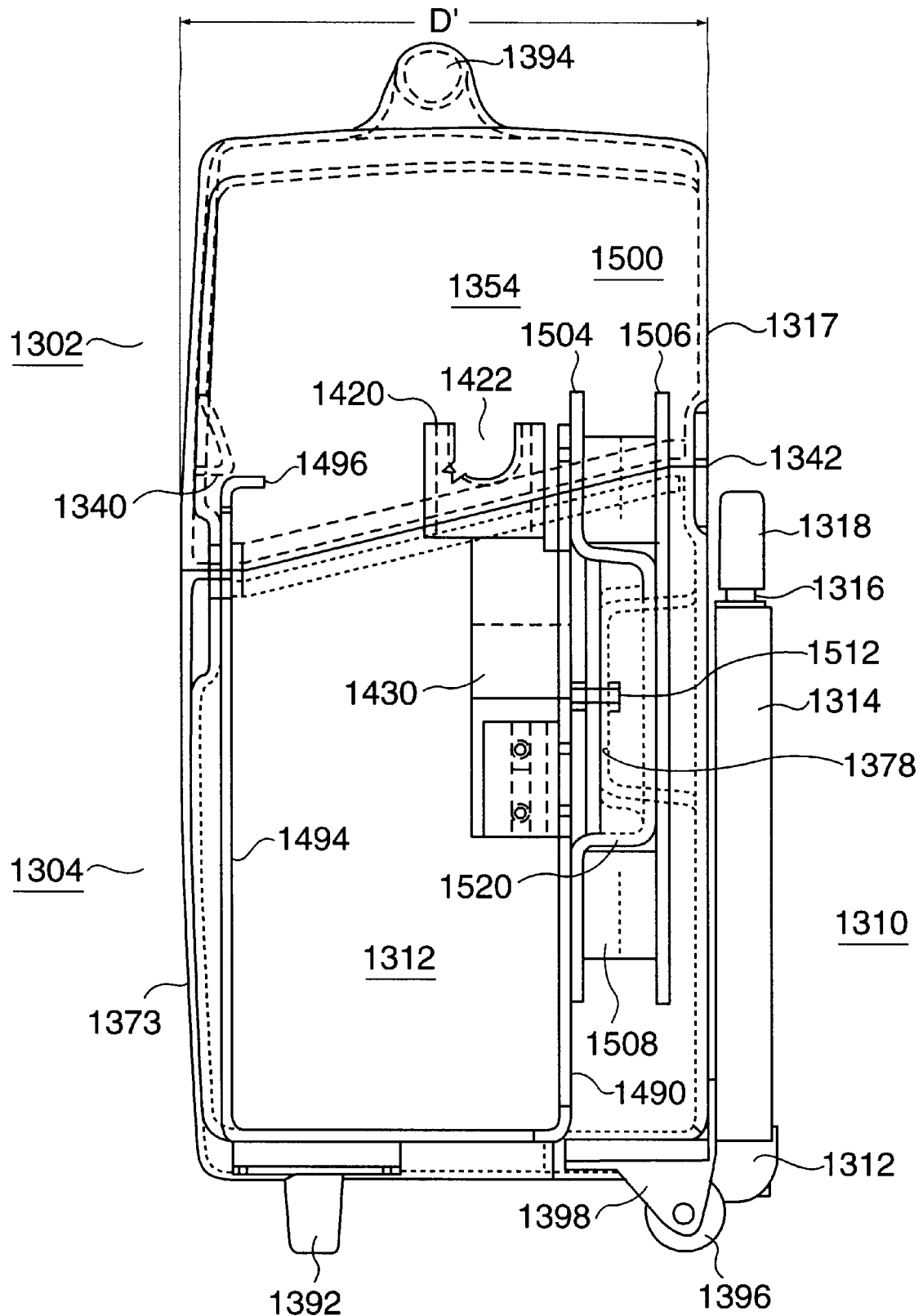
FIG. 13c is a right side view of a third embodiment of the case of the present invention.
Figure 13D:
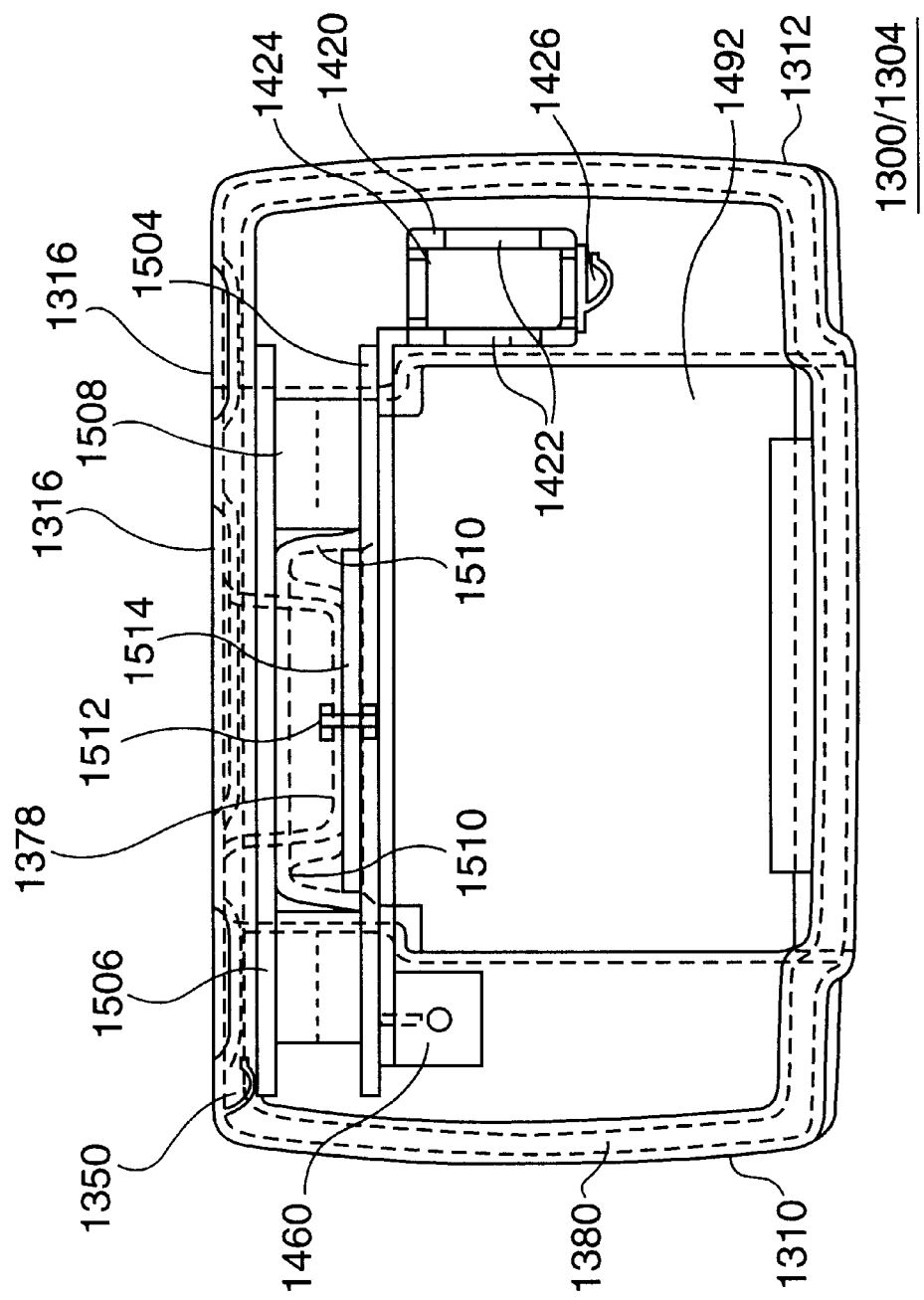
FIG. 13d is a plan view of the main body section of the case of the present invention including a main body insert and a drum assembly.

FIG. 13a is a front view, FIG. 13b is a rear view, and FIG. 13c is a right side view of a third embodiment 1300 of the case of the present invention. FIG. 13d is a plan view of the main body section of the case 1300 of the present invention including a main body insert 1400 and a drum assembly 1500. The third embodiment of the case 1300 of the present invention is similar to that of the first embodiment of the case 100 of the present invention but differs mainly in that: (i) the third embodiment uses a one-piece main body section rather than a "clamshell" two-piece main body section; (ii), in the third embodiment, the rotatable drum or reel for accommodating an insertion tube is mounted on the inside surface of the rear wall of the main body section rather than on the inside surface of the front wall of a hinged case body section; and (iii) in the third embodiment, a removable main body insert (also referred to as a "peripheral carriage") is provided in the main body section to hold a combined light source and camera control unit. The wheels and telescoping handle system discussed below with respect to the third embodiment may be used in the first or second embodiments. Further, the materials used for the shell of the case and the mating tongue and groove aluminum pieces provided on the edges of case components, discussed above with reference to the first embodiment, may be used in the second and third embodiments as well. Furthermore, as will be apparent to those skilled in the art, certain features of all three embodiments may be combined to create still further embodiments.

Referring first to FIGS. 13a through 13c, the third embodiment of the case 1300 of the present invention includes a lid 1302 and a main body section 1304. As shown in FIGS. 13b and 13c, the lid 1302 is pivotably coupled with the main body section 1304 by means of a pivotable connection means, such as torque hinges 1342 for example. When the lid 1302 is closed onto the main body section 1304, fastening means, such as latches 1380 for example, may be employed to prevent the lid 1302 from pivoting open. As was the case in the first embodiment of the case of the present invention discussed above, the lid 1302 of the third embodiment can accommodate a flat panel display screen. Although compressible foam may be used to hold a flat panel display screen, other means for holding the flat panel display screen within the lid, such as a latching system, a snap lock system, velcro, etc. may be employed. As shown in FIG. 13d, the lid 1302 may include a clip 1350 for holding a cable of the video monitor (not shown).

The main body section 1304, and thus the case 1300, is supported by feet 1392 at its front and wheels 1396 at its rear. The wheels 1396 are rotatably coupled with wheel mounts 1398. The wheel mounts 1398 are fastened (using any one of a number of known techniques) to the main body section 1304 of the case 1300.

The top of the lid 1302 is provided with a handle 1394 for transporting of the case 1300. The handle 1394 is particularly useful for transporting the case 1300 when it is empty. However, if the case 1300 is filled with a remote visual inspection system and certain peripheral components discussed above, it may become fairly heavy such that transporting the case 1300 using the handle 1394 may become cumbersome. A telescoping handle system 1310, in conjunction with the wheels 1396, facilitate transport of the case 1300, particularly when the case 1300 is filled with a remote visual inspection system and/or peripheral components. As shown in FIGS. 13b and 13c, the telescoping handle system 1310 is mounted to the main body section 1304 of the case 1300 by means of a mounting unit 1312. Two (2) parallel stationary outer cylinders 1314 are mounted to the mounting unit 1312, and thus to the main body section 1304 of the case 1300. A handle 1318 is connected to two (2) cylinders 1316 which fit within the stationary outer cylinders 1314 and which can telescope with respect to the stationary outer cylinders 1314. Means, known to those skilled in the art, are employed to control and limit the telescoping of the inner cylinders 1316 with respect to the outer cylinders 1314 and to permit the position of the inner cylinders 1316 to lock with respect to the stationary outer cylinders 1314. When the handle 1318 is pulled up by a user and the inner cylinders 1316 extend from the stationary outer cylinders 1314, the case 1300 can be tipped back so that the feet 1392 are lifted and the case 1300 is supported by the wheels 1396.

Figure 11A:
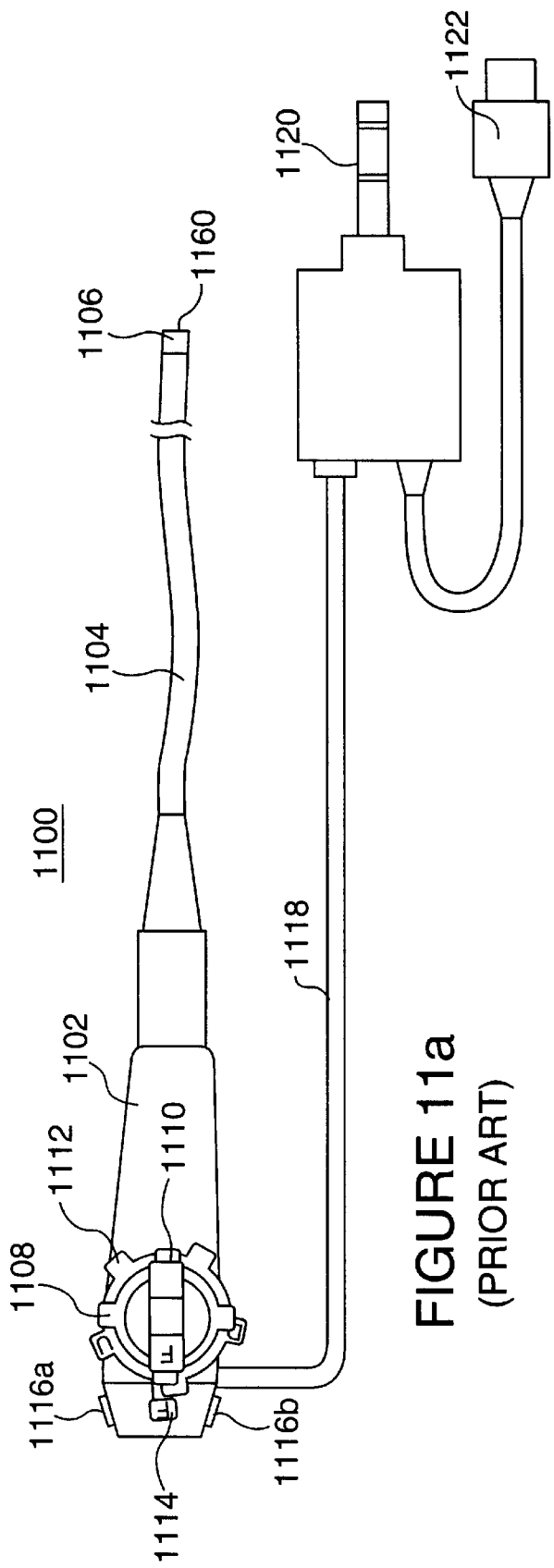
FIG. 11a is a side view of a conventional videoimagescope.

Referring now to FIGS. 13c, 13d, and FIGS. 14a through 14c, the main body insert (or "peripheral carriage") 1400 will now be described. The main body insert 1400 serves to, inter alia, safely accommodate a camera control unit connector (See e.g., FIG. 11a, element 1122), a light guide connector (See e.g., FIG. 10a, element 1018 and FIG. 11a, element 1120), a integrated light source and camera control unit (e.g., an "ILVC"), etc. As shown in side views of FIGS. 13c and 14c, the main body insert 1400 includes a rear plate 1490, a bottom plate 1492, and a front plate 1494. Each will be described below.

As shown in FIGS. 14a through 14c, a handle opening 1498 is defined the front plate 1494 of the main body insert 1400. Although not shown in the Figures, the rear plate 1492 of the main body insert 1400 may also define a handle opening. The handle opening(s) 1498 permit the main body insert 1400 to be easily lifted from the main body section 1304 of the case 1300. A top edge of the front plate 1494 of the main body insert 1400 includes a rearward extension 1496 which serves to contain the movement of peripheral equipment accommodated in the main body insert 1400. As shown in FIGS. 13c and 13d, the front surface of the front plate 1494 of the main body insert 1400 roughly follows the inner surface of the front surface 1373 of the main body section. Referring now specifically to FIG. 13c, an inwardly projecting lid lip 1340 on the front surface 1350 of the lid 1302 of the case 1300 will contact the rearward extension 1496 of the main body insert 1400 such that the main body insert 1400 is held in place when the lid 1302 is closed over the main body section 1304 of the case 1300.

A first side of the rear plate 1490 of the main body insert 1400, as shown in FIGS. 13c, 13d, and 14a through 14c, includes a forward projecting plate 1491. A plate 1429 of a camera control unit ("CCU") connection holder 1420 is coupled with the forward projecting plate 1491, via a spacer plate 1470, by means of machine screws 1428 for example. Semicircular cutouts 1422, shaped to accommodate a CCU connector (See e.g., FIG. 11a, element 1122) are defined in two parallel plates of the CCU connection holder 1420. Referring now to FIG. 13d, a velcro strap 1424 is used to contain a CCU connector accommodated in the CCU connection holder 1420. Finally, the CCU connection holder 1420 includes a clip 1426 for holding a power cable for the CCU associated with the CCU connector.

A light guide connector holster 1460 is connected, via machine screws 1462 for example, to another side of the rear plate 1490 of the main body insert 1400. The light guide connector holster 1460 may be a block of machined metal or other material having a (e.g., cylindrical) void defined in a top surface thereof. The void is shaped to accommodate a light guide connector (See e.g., FIG. 10a, element 1018 and FIG. 11a, element 1120).

The main body insert (or peripheral carriage) 1400 is adapted to securely hold peripheral equipment (e.g., a combined light source and camera control unit or ("ILVC")) of a remote visual inspection system. More specifically, a box-shaped ILVC can be contained by rear plate 1490, bottom plate 1492, front plate 1494, CCU mounting plate 1491, and the light guide connector holster 1460. Front plate ledge 1496 further contains the movement of the ILVC. Preferably, all controls and connection ports of the ILVC (or of other peripheral equipment accommodated by the main body insert 1400) will be exposed at the open top of the main body insert 1400. Referring now to FIG. 14c, when the main body insert 1400 is removed from the main body section 1304 of the case 1300, it may be flexed in response to applied force such that the back and/or rear plates 1494 and 1490 move in the direction shown by arrows E. Once the main body insert 1400 is flexed to such an extent that the box-shaped ILVC can clear the front plate ledge 1496, the ILVC can be removed from the main body insert 1400 via the top of the main body insert 1400.

As shown in FIG. 13c, a void is defined between the rear plate 1490 of the main body insert 1400 and a rear surface 1317 of the main body section 1304 of the case 1300. A drum assembly 1500, described below, is accommodated in this void.

Figure 11B:
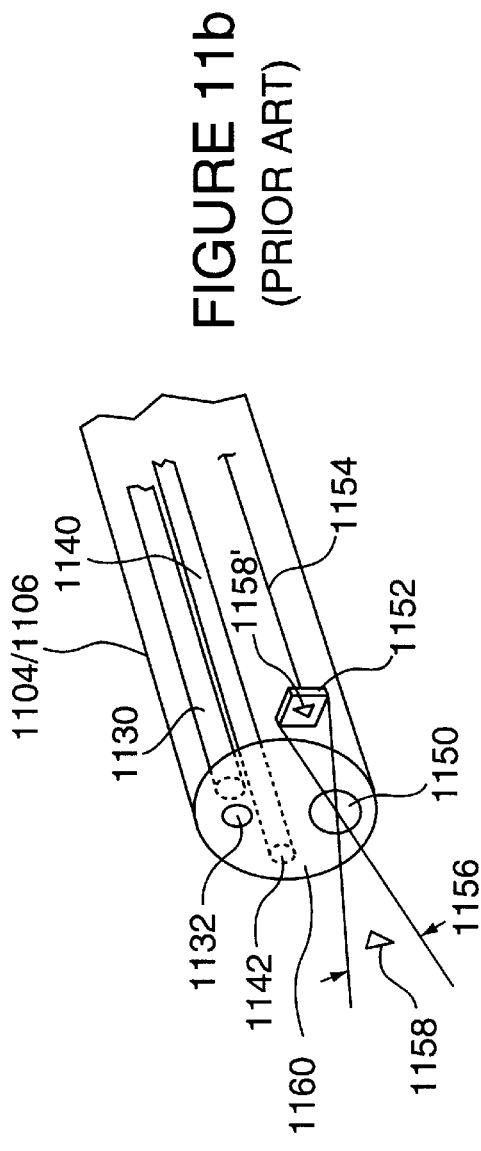

FIG. 16a is a plan view, FIG. 16b is a front end view, and FIG. 16c is a side view of an alternative main body insert (also referred to as a "peripheral carriage") 1400' for use with a simple case. Since the alternative main body insert 1400' is similar to the main body insert 1400 of FIGS. 14a through 14c, like reference numerals have been used to label like elements. The alternative main body insert 1400' differs from the main body insert 1400 in that it further includes an insertion tube reel (or drum) 1610 and an endoscope body (see, e.g., 1002 of FIG. 10 and 1103 of FIG. 11) holster 1650. The alternative main body insert 1400' is advantageous because the design of a case in which the insert 1400' may be used is simplified. For example, since the reel 1610 is rotatably coupled with the carriage 1400' rather than the case, soft cases or bags may be used to carry the system.

As shown in the plan view of FIG. 16a, the insertion tube reel 1610 includes a drum arranged between a rear plate 1612 and a front plate 1614. The reel 1610 may include a cylindrical recess 1616. The reel 1610 may be rotatably coupled with the rear plate 1490 by means of a bolt 1618 and connector 1620 for example. Although the end of the bolt 1618 is shown as projecting forward from the inside surface of the rear plate 1490, it may be fit into a recess (not shown) in the inside surface of the rear plate such that it is flush with, or below, the inside surface of the rear plate 1490. As shown in the front end view of FIG. 16b and the side view of FIG. 16c, the reel 1610 may extend above the front 1494 and rear 1490 plates of the reel 1610.

As shown in the plan view of FIG. 16a, the endoscope body holster 1650 may include relatively rigid outer walls 1652, a relatively rigid floor 1656, and inner walls 1654 formed of a compressible inner material (e.g., foam). As can be seen from FIGS. 16a through 16c, the endoscope body holster 1650 may be arranged below and behind the CCU holder 1420.

Figure 17B:
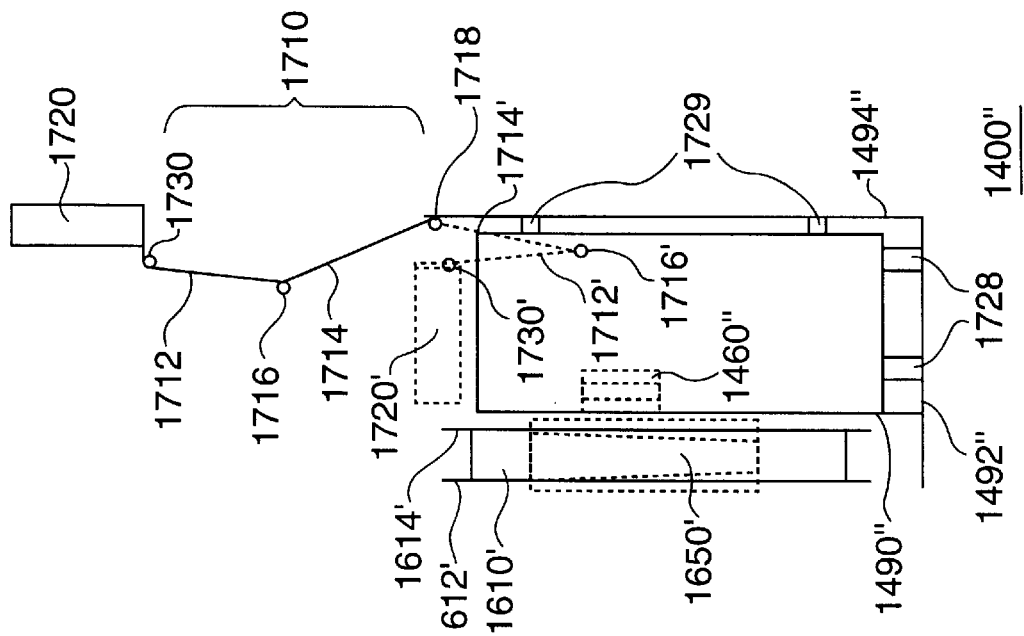
FIG. 17b is a side view, of another alternative main body insert (also referred to as a "peripheral carriage") similar to that shown in FIGS. 14a–14c but here too for use with a simple case.
Figure 17A:
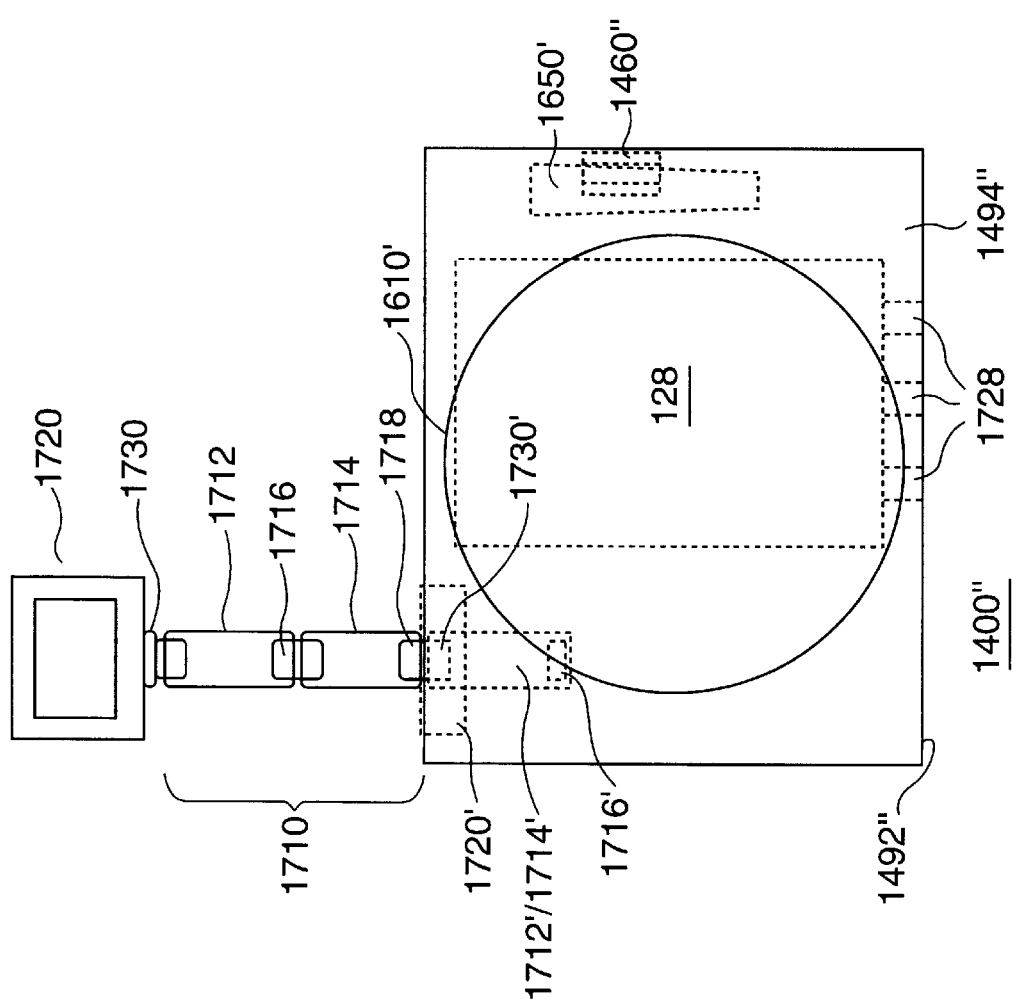
FIG. 17a is a front view.

FIG. 17a is a front view, and FIG. 17b is a side view, of another alternative main body insert (also referred to as a "peripheral carriage") 1400" for use with a simple case. Since this alternative main body insert 1400" is similar to those 1400 and 1400' of FIGS. 14a through 14c and 16a through 16c, respectively, like reference numerals have been used to label like elements. This alternative main body insert 1400" differs from the alternative main body insert 1400' of FIGS. 16a through 16c in that it further includes a video display screen (e.g., an LCD) 1720 and a screen positioning assembly 1710.

The screen positioning assembly 1710 includes an upper arm 1712 and a lower arm 1714 which are pivotally coupled, for example by means of a torque hinge 1716. Similarly, the lower arm 1714 is pivotally coupled, by means of a torque hinge 1718 for example, with a rear plate 1490" of the peripheral carriage 1400" and the upper arm 1712 is pivotally coupled, by means of a torque hinge 1730 for example, to the video display screen 1720.

As shown in FIGS. 17a and 17b, the upper and lower arms 1712' and 1714', respectively, may be folded, the video screen 1720' arranged flat, and the lower arm 1714' pivoted within the front wall 1494" such that the screen positioning assembly 1710' and the video display screen 1720' are arranged within a volume defined by the front and rear plates 1494" and 1490" of the peripheral carriage 1400", to the left of a CCU and light source unit 128. This state may be referred to as a "collapsed" or "transport" state. When deployed, the screen positioning assembly 1710 may position the video display screen 1720 above the front and rear plates 1494" and 1490", respectively, of the peripheral carriage 1400". This state may be referred to as an "extended" or "deployed" state.

Feet 1728 and 1729 of the CCU and light source unit 128 serve to define an air flow void between the CCU and light source unit 128 and adjacent plates of the peripheral carriage 1400". Further, if the peripheral carriage 1400" is metal, it serves as a heat sink for heat generated by the CCU and light source unit 128.

Figure 15B:
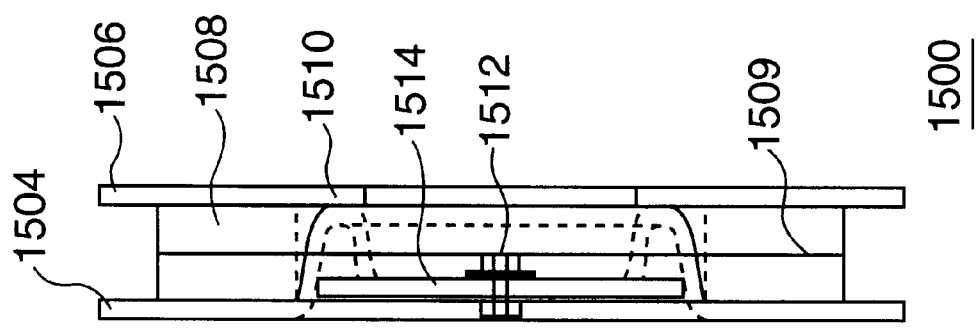
FIG. 15b is a side view of a drum assembly for the case of FIGS. 13a through 13d.
Figure 15A:
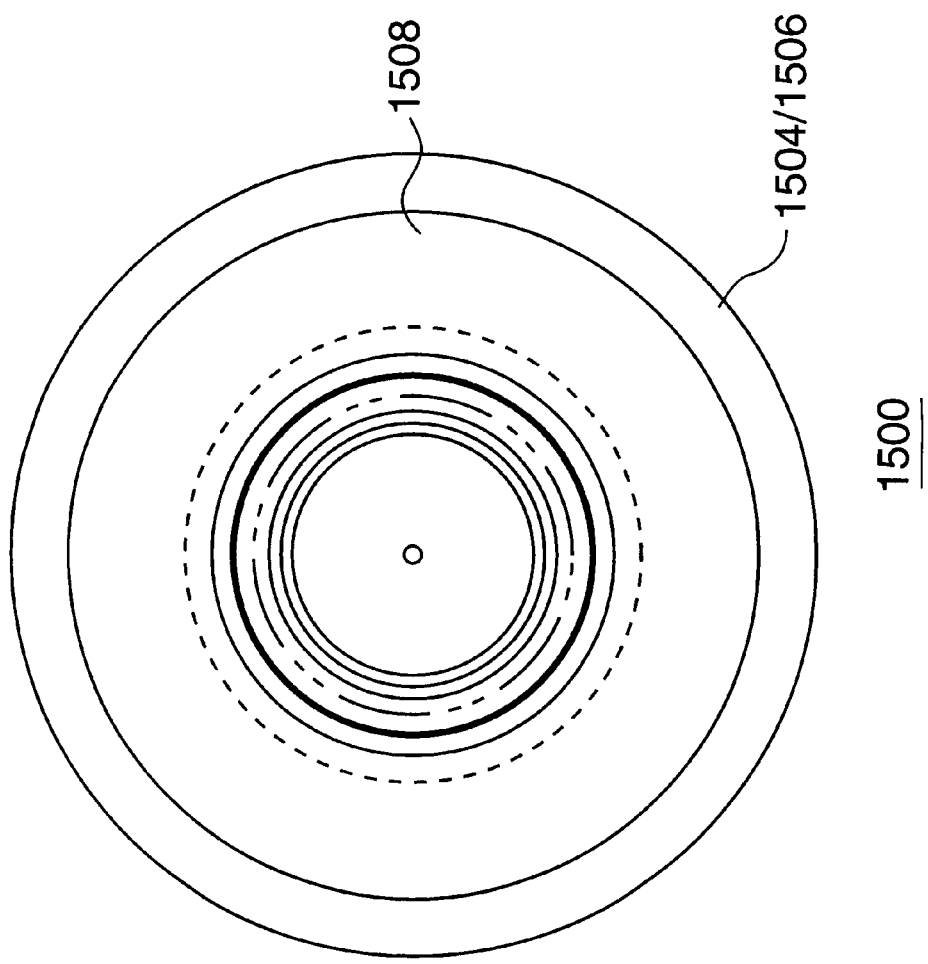
FIG. 15a is a front end view.

Assuming that the main body insert 1400 is to be used, the drum assembly 1500, and its relationship with the main body section 1304 of the case 1300 is described referring to FIGS. 13b through 13d, 15a, and 15b. The purpose of the drum is to enable an insertion tube (See e.g., FIG. 10a, element 1004 and FIG. 11a, element 1104) of a remote visual inspection system to be easily stored, transported, and deployed. Referring first to FIG. 15b, the drum assembly 1500 may include a front drum plate 1504 and a rear drum plate 1506. The front drum plate 1504 may curve towards then away from the rear drum plate 1506 as it moves radially inward as is shown by bends 1510.

As is further shown, the front drum plate 1504 may be attached to a mounting plate 1514. Referring now to FIGS. 13b through 13d, the mounting plate 1514 may be rotatably connected with the (e.g., circular) indent 1378 of the back 1317 of the main body section 1304 of the case 1300. This connection may be effected with a bolt 1512 for example. The means for effecting the rotatable connection may be an easily removable means (e.g., a pin having a ball detent) to facilitate removal and installation of the drum assembly 1500 from and into, respectively, the main body section 1304 of the case 1300. When the lid 1302 of the case 1300 is shut, foam in the lid 1302 may compress against the front drum plate 1504 and/or the rear drum plate 1506 such that free rotation of the drum assembly 1500 is prevented.

An annular foam section 1508 may be provided between the front and rear drum plates 1504 and 1506 to cushion an insertion tube wound thereon. Recall that the distal end of the insertion tube may include a tip adapter including optical and/or electro-optical elements. To protect this relatively delicate tip adapter, a slot 1509 is provided in the annular foam section 1508 so that the distal tip of the insertion tube may be pushed into the annular foam section 1508 so that the tip adapter is securely held when the remote visual inspection system is being held and/or transported.

When the lid 1302 is opened, the video display monitor (not shown) can be viewed, controls and connection ports at the top of the peripheral equipment can be accessed easily, and connectors can be accessed easily. Thus, once the case 1300 is transported to a field site, the remote visual inspection system may be deployed quickly. Moreover, when done, the remote visual inspection system can be stored quickly. Finally the case 1300 can accommodate a flat panel display monitor, peripheral equipment, and a relatively long insertion tube.

What is claimed is:

1. A portable remote visual inspection system comprising:
    a) a remote visual inspection system including an endoscope; and
    b) a case, the case including
        i) a first section accommodating a light source for providing light to the remote visual inspection system, and
        ii) a second section, coupled with the first section, and accommodating the endoscope, wherein the second section includes a drum, the drum being rotatable with respect to the case and holding a flexible insertion tube of the remote visual inspection system.

2. A portable reel for holding an insertion tube of a remote visual inspection system, the portable reel comprising:
    a) a case body defining a cavity;
    b) a reel for holding the insertion tube, the reel being rotatably coupled with the case body such that, at any given time, a first portion of the reel is located within the cavity defined by the case body and a second portion of the reel extends outside of the cavity defined by the case body; and
    c) a lid adapted for covering the case body and the reel.

3. The portable reel of claim 2 wherein the lid is pivotably coupled with the case body.

4. The portable reel of claim 3 wherein, when the lid is shut so as to cover the case body, the lid prevents the reel from rotating with respect to the case body.

5. The portable reel of claim 2 wherein, when the lid is shut so as to cover the case body, the lid prevents the reel from rotating with respect to the case body.

6. The portable reel of claim 2 wherein the case body includes
    i) a front wall,
    ii) a back wall,
    iii) a left side wall arranged between the front and back walls, and
    iv) a right side wall arranged between the front and back walls,
        wherein the front, back, left side, and right side walls define an upper end of the case body and a lower end of the case body, the lower end of the case body being closed by a bottom surface,
        wherein the back wall is taller than the front wall such that the left and right walls are tapered, and
        wherein the reel is rotatably coupled with the front wall.

7. The portable reel of claim 6 wherein the lid includes
    i) a back wall, pivotably coupled with the back wall of the case body,
    ii) front wall,
    iii) a left side wall arranged between the front and back walls of the lid, and
    iv) a right side wall arranged between the front and back walls of the lid,
        wherein the front, back, left side, and right side walls of the lid define an upper end of the lid and a lower end of the lid, the upper end of the lid being closed by a top surface, and
        wherein the front wall of the lid is taller than the back wall of the lid such that the left and right walls of the lid are tapered.

8. A device for transporting and storing a remote visual inspection system, the device comprising:
    a) a case body, the case body configured to accommodate a light source and an insertion tube, wherein the case body includes
        i) a main body section configured to accommodate the light source, and
        ii) a hinged body section, pivotably coupled with the main body section, and configured to accommodate the insertion tube; and
    b) a lid, pivotably couplable with the case body and configured to accommodate a video display monitor.

9. The device of claim 8 wherein the hinged body section includes a reel, rotatably coupled with an inside surface of the hinged body section, the reel configured to accommodate the insertion tube.

10. The device of claim 8 wherein the main body section includes
    i) a back wall,
    ii) a left side wall adjacent to the back wall,
    iii) a right side wall adjacent to the back wall,
    iv) a floor adjacent to the back, left side, and right side walls, and
    v) an insert, the insert having an outer surface shaped to fit within the back wall, the left side wall, the right side wall, and the floor, and having a first inside surface configured to accommodate the light source, and
wherein the hinged body section includes
    i) a front wall,
    ii) a left side wall adjacent to the front wall,
    iii) a right side wall adjacent to the front wall,
    iv) a floor adjacent to the front, left side, and right side walls of the hinged body section, and
    v) a reel, the reel rotatably coupled with the front wall of the hinged body section and adapted to accommodate the insertion tube.

11. The device of claim 10 wherein the insert includes at least one indent to accommodate at least one of (i) an auxiliary video connector, (ii) light source connectors, and (iii) a camera control unit connector.

12. The device of claim 10 wherein the insert is shaped such that, when a light source is accommodated by the insert, connection ports and controls of the light source are visible and accessible.

13. The device of claim 10 wherein the floor of the main body section is pivotably coupled with the floor of the hinged body section.

14. The device of claim 10 wherein the lid includes
    i) a front wall,
    ii) a back wall,
    iii) a left side wall arranged between the front and back walls of the lid,
    iv) a right side wall arranged between the front and back walls of the lid,
    v) a top surface, closing a top edge of the front, back, left side, and right side walls of the lid, and
    vi) an insert, the insert of the lid having an outer surface shaped to fit within a cavity defined by the front wall, the back wall, the right wall, the left wall, and the top surface of the lid, and having an inner surface shaped to accommodate the video display monitor.

15. The device of claim 14 wherein at least one of the insert of the lid and the insert of the main body section is a foam insert.

16. The device of claim 14 wherein the device has:
i) a first state in which
 (A) the hinged body section is closed against the main body section such that the left wall of the hinged body section abuts the left wall of the main body section and the right wall of the hinged body section abuts the right wall of the main body section, and
 (B) the lid is closed against the case body such that the left wall of the lid abuts the left walls of the main body section and the hinged body section, the right wall of the lid abuts the right walls of the main body section and the hinged body section, and the front wall of the lid abuts the front wall of the hinged body section; and
ii) a second state in which
 (A) the hinged body section is closed against the main body section such that the left wall of the hinge body section abuts the left wall of the main body section and the right wall of the hinged body section abuts the right wall of the main body section, and
 (B) the lid is opened from the case body such that the left wall of the lid is separated from the left walls of the main body section and the hinged body section, the right wall of the lid is separated from the right walls of the main body section and the hinged body section, and the front wall of the lid is separated from the front wall of the hinged body section.

17. The device of claim 14 wherein the device has:
i) a first state in which
 (A) the hinged body section is closed against the main body section such that the left wall of the hinged body section abuts the left wall of the main body section and the right wall of the hinged body section abuts the right wall of the main body section, and
 (B) the lid is closed against the case body such that the left wall of the lid abuts the left walls of the main body section and the hinged body section, the right wall of the lid abuts the right walls of the main body section and the hinged body section, and the front wall of the lid abuts the front wall of the hinged body section;
ii) a second state in which
 (A) the hinged body section is closed against the main body section such that the left wall of the hinged body section abuts the left wall of the main body section and the right wall of the hinged body section abuts the right wall of the main body section, and
 (B) the lid is opened from the case body such that the left wall of the lid is separated from the left walls of the main body section and the hinged body section, the right wall of the lid is separated from the right walls of the main body section and the hinged body section, and the front wall of the lid is separated from the front wall of the hinged body section; and
iii) a third state in which
 (A) the hinged body section is opened from the main body section such that the left wall of the hinged body section is separated from the left wall of the main body section and the right wall of the hinged body section is separated from the right wall of the main body section, and (B) the lid is opened from the case body such that the left wall of the lid is separated from the left walls of the main body section and the hinged body section, the right wall of the lid is separated from the right walls of the main body section and the hinged body section, and the front wall of the lid is separated from the front wall of the hinged body section.

18. The device of claim 17 wherein, when the case is in its first state, the insert of the lid is compressed by the reel of the hinged body section.

19. The device of claim 17 wherein, when the case is in its first state, the insert of the lid is compressed by the reel of the hinged body section and the insert of the main body section is compressed by the reel of the hinged body section, and
wherein, when the case is in its second state, the insert of the main body section is compressed by the reel of the hinged body section.

20. A device for transporting and storing a remote visual inspection system, the device comprising:
a) a case body, the case body configured to accommodate a light source and an insertion tube;
b) a lid, pivotably couplable with the case body and configured to accommodate a video display monitor; and
(c) a removable drum for accommodating an insertion tube of a remote visual inspection system.

21. The device of claim 20 wherein the removable drum includes a front plate, a rear plate, and an annular element arranged between the front and rear plates of the removable drum.

22. The device of claim 21 wherein the annular element is compressible foam.

23. The device of claim 21 wherein a slot is defined in the annular element.

24. A peripheral carriage comprising
a) a front plate;
b) a rear plate;
c) a bottom plate arranged between the front and rear plates;
d) a removable drum for accommodating an insertion tube of a remote visual inspection system, the removable drum being rotatably coupled with one of (a) the front plate and (b) the rear plate; and
(e) a video display screen which is coupled with one of (a) the front plate or (b) the rear plate and which may be positioned with respect to the one of the front plate and the rear plate.

25. The device of claim 24 further comprising a screen positioning assembly arranged between the video display screen and the one of the front plate and the rear plate.

26. The device of claim 25 wherein the screen positioning assembly includes
(i) a lower arm having a first end pivotally coupled with the removable case body insert and a second end, and
(ii) an upper arm having a first end pivotally coupled with the second end of the lower arm and a second end pivotally coupled with the video display screen.

27. A device for transporting and storing a remote visual inspection system, the device comprising:
a) a case body, the case body configured to accommodate a light source and an insertion tube; and
b) a lid, pivotably couplable with the case body and configured to removably accommodate, within the lid, a video display monitor, wherein the lid has:

1) a front wall;
2) a back wall;
3) a left side wall arranged between the front and back walls;
4) a right side wall arranged between the front and side walls;
5) a top surface, closing a top edge of the front, back, left side and right side walls; and
6) an insert, the insert having an outer surface shaped to fit within a cavity defined by the front wall, the back wall, the right wall, the left wall, and the top surface, and having an inner surface shaped to accommodate the video display monitor.

28. A device for transporting and storing a remote visual inspection system, the device comprising:
   a) a case body, the case body configured to accommodate a light source and an insertion tube;
   b) a lid, pivotably couplable with the case body and configured to accommodate, within the lid, a video display monitor; and
   c) a removable case body insert for accommodating peripheral devices, wherein the removable case body insert has a connector holder.

29. A device for transporting and storing a remote visual inspection system, the device comprising:
   a) a case body, the case body configured to accommodate a light source and an insertion tube;
   b) a lid, pivotably couplable with the case body and configured to accommodate, within the lid, a video display monitor; and
   c) a removable case body insert for accommodating peripheral devices, wherein the removable case body insert has a front plate, a rear plate, and a bottom plate arranged between the front plate and the rear plate.

30. The device of claim 29 wherein at least one of the front plate and rear plate of the removable case body insert has a handle.

31. The device of claim 29 wherein the front plate of the removable case body insert includes a rearwardly extending ledge, and
   wherein an inside surface of a front section of the lid includes a lip which abuts the ledge of the front plate of the removable case body insert when the lid is closed upon the case body.

32. The device of claim 29 wherein the removable case body insert further includes a reel for accommodating an insertion tube, the reel being rotateably coupled with the rear plate of the removable case body insert.

33. The device of claim 32 wherein the removable case body insert further includes a holster for accommodating an endoscope body.

* * * * *